into a sample cell, containing the majority of said fluid and disposed substantially within the path of radiation from an irradiating means, by squeezing it between two windows; subjecting said sample cell to radiation of fixed intensity and distinct but selectable frequency; and measuring photometrically the intensity of the transmitted radiation.

11. The method of claim 10 which further comprises wetting the surfaces of said test pouch which are in contact with said windows with a contact fluid.

12. The apparatus of claim 1 wherein said radiation detection means is a photocell.

13. Photometric means for monitoring the chemical composition of a reaction mixture held within a reaction compartment of a flexible disposable chemical testing container comprising radiation source means adjacent a first side of the reaction compartment, means adjacent the opposite side of the reaction compartment responsive to the magnitude of light absorbed by the reaction mixture as electromagnetic radiation is transmitted therethrough from said radiation source means, and means to press said radiation source means and said responsive means against opposite sides of the reaction compartment during analysis to define a fixed optical path length through the reaction mixture.

14. Photometric means for monitoring the chemical composition of a reaction mixture held within a reaction compartment of a flexible disposable chemical testing container comprising radiation source means adjacent a first side of the reaction compartment, means adjacent the opposite side of the reaction compartment responsive to the magnitude of light absorbed by the reaction mixture as electromagnetic radiation is transmitted therethrough from said radiation source means, and means to deform the flexible wall or walls of the reaction compartment, during analysis, to define a fixed optical path length through the reaction contained therein.

* * * * *

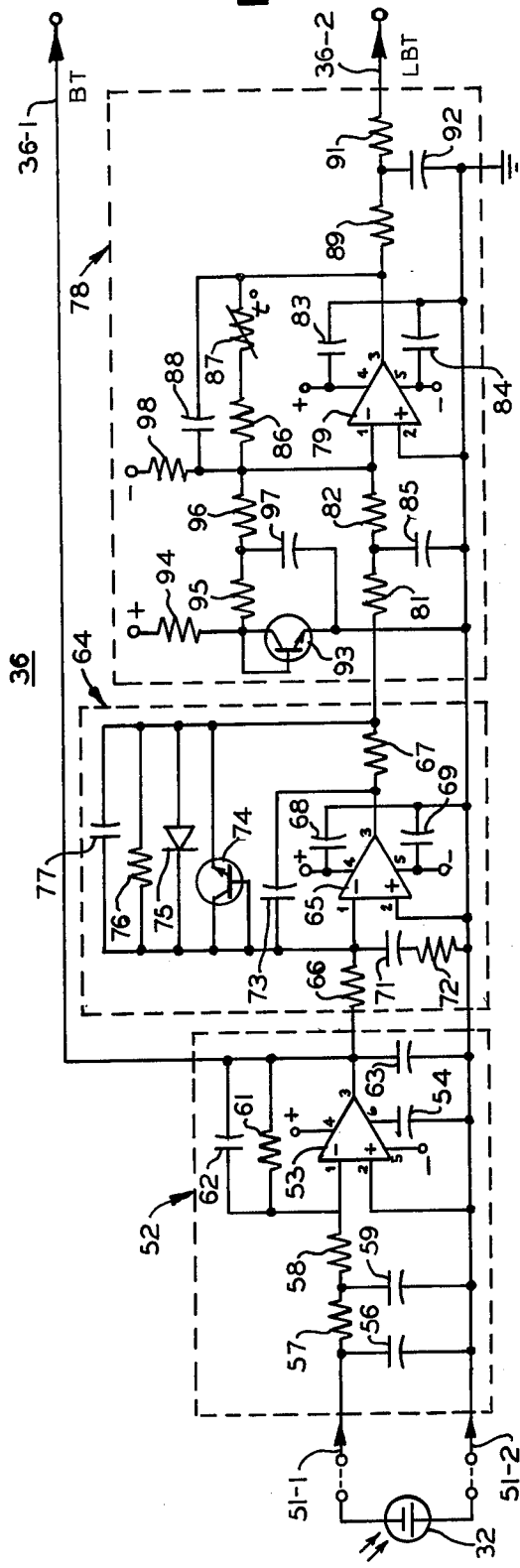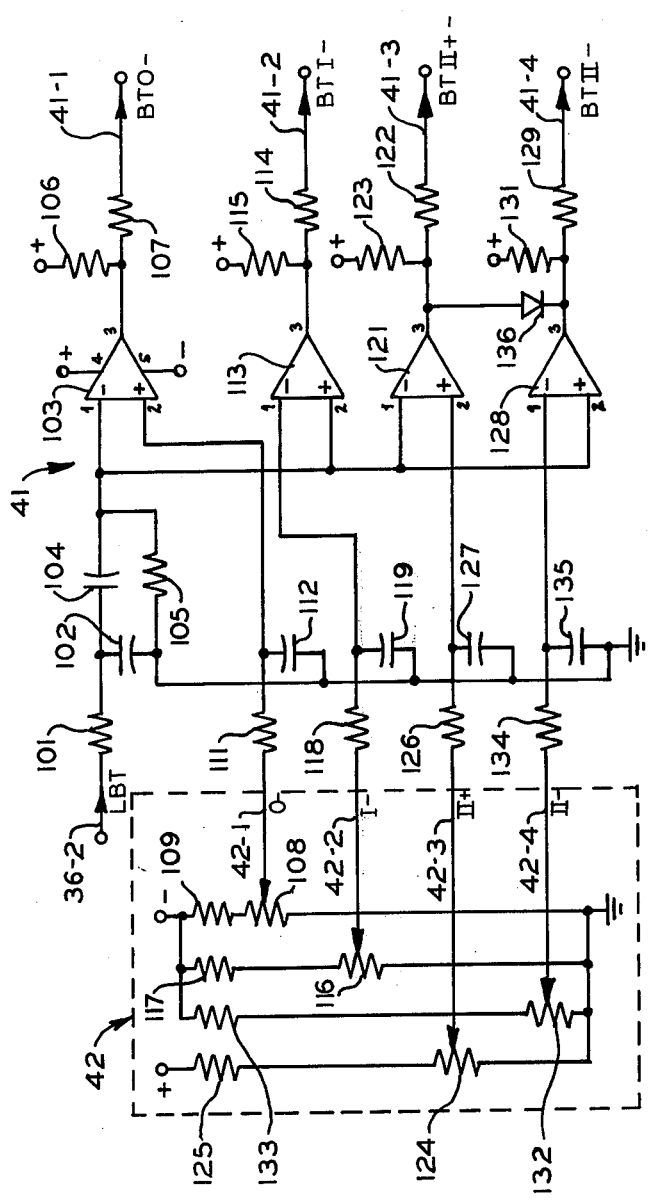

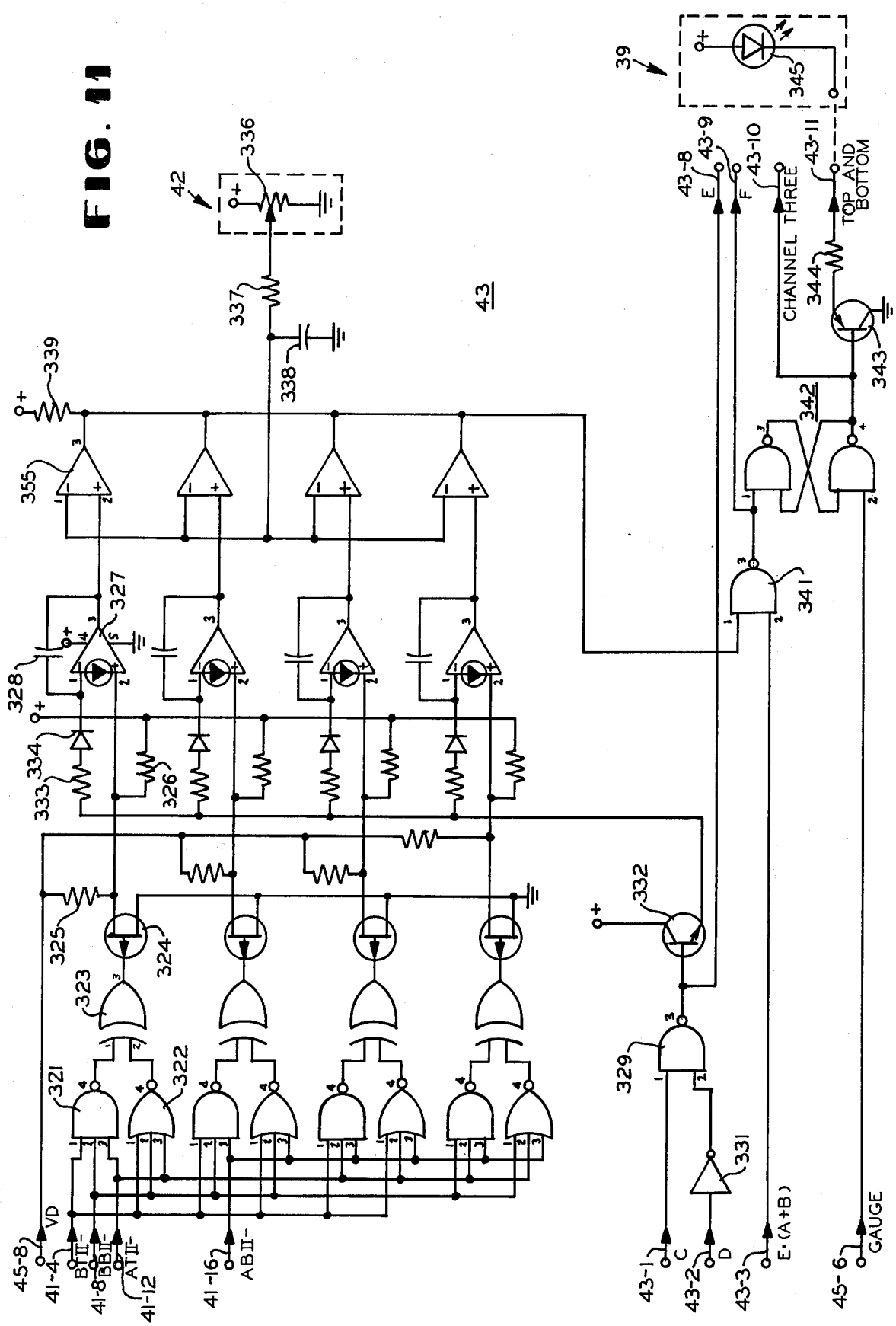

APPARATUS AND METHOD FOR INSPECTING GLASS CONTAINERS

BACKGROUND OF THE INVENTION

1. Field of the Invention

The present invention relates in general to the inspection of glass containers and more particularly to the inspection of wide mouth glass containers for ribbon tear defects.

2. Description of the Prior Art

Glass containers are typically formed by forcing a gas into the interior of a ball of semi-molten glass in a mold. The glass ball expands against the interior surfaces of the mold to form a bottom, side walls and an annular rim defining an opening of the container. During the forming process, various types of defects can also be formed some of which require the container to be rejected. At first, the containers were manually inspected by the human eye but this method proved to be costly, time consuming and inaccurate. Thus, automatic inspection devices were employed in order to reduce the inspection cost and increase the reliability of the inspection process. A typical inspection device is disclosed in U.S. Pat. No. 3,880,750 issued to Richard L. Butler and John W. Juvinall on Apr. 29, 1975 and assigned to Owens-Illinois, Inc. That device inspects the sealing surface of a glass container which is rotated past a light source focused on the sealing surface. A light sensor receives light reflected from the rim to generate an output signal having a magnitude proportional to the amount of received light. A defect will cause a deviation from the d. c. signal level wherein the signal is amplified and filtered to remove the d. c. component. Different types of defects generate different signal levels which are compared with reference signals to identify the various types of defects and generate a defective container signal in response to such a detection.

Another type of defect which generally occurs in the side walls of wide mouth containers is the so-called ribbon tear defect. Such a defect has at least a portion thereof defined by spaced apart edges and has light transmitting properties which differ from those of the side walls. Although it is not fully understood how such defects are formed, one theory is that a portion of the side wall sticks to the interior of the mold as the container is removed. Since most molds are split into two halves along the vertical axis of the container, a pair of seams spaced approximately 180° apart are formed on the side walls. Although the ribbon tear defects often look like the seams, the seam spacing cannot be utilized to distinguish between the tears and the seams because some seams are too thin to generate a reliable signal from a light source and detector system. Therefore, a prior art light source and detector device was made to reject a container only upon a detection which resulted in a large reduction in the d. c. signal level. Although such a device would reject many ribbon tear defects, it would also reject some relatively heavy seams and would not reject some small ribbon tear defects.

SUMMARY OF THE INVENTION

The present invention is directed to an apparatus and method for detecting ribbon tear defects in wide mouth glass containers. The container, mounted in an inspection machine, has its interior illuminated by a light source and is rotated past a detector assembly. The detector assembly includes four photovoltaic cells mounted along a vertical line parallel to the vertical axis of the container. The cells are mounted in an upper pair and a lower pair to reduce the effect of electrical noise caused by imperfections in the glass and are responsive to the amount of light transmitted through the side wall of the container to generate output signals having a magnitude proportional to the amount of light received. Each cell output signal is the input to an associated amplifier which pre-amplifiers, logarithmically amplifies and amplifies the signal. The output from each amplifier is filtered to remove the d. c. component to obtain a signal having a magnitude proportional to the percentage change in the d. c. signal level caused by a seam or a defect. Thus, the filtered signal is free from the effects of different distances between the light source and the cells, dirt on the cells and differences in the output signal level for the same amount of received light so that the light source, cells and amplifiers do not have to be recalibrated during use.

Each filtered signal is then compared with one of four reference signals levels, a 0− level representing a severe or large signal reduction, a I− level representing a normal or average signal reduction, a II− level representing a small signal reduction and a II+ level representing a small signal increase from a focusing type of defect. The comparison circuits each generate logic signals representing the absence or presence of a detection at the respective signal levels. Detector circuits monitor the logic signals for characteristics such as signal duration and the relative timing between signals in order to distinguish among seams, small defects and ribbon tear defects such that a container is rejected when a ribbon tear defect is present. The detector circuits determine if the logic signals satisfy a first condition that at least one of the pairs of cells has responded to a detection of at least the normal signal level, and one of three other conditions. The other conditions are a second detection of at least the normal signal level by at least one of the cells within 150° of rotation of the container from the first detection, a detection of at least a predetermined width of at least the normal signal level and a detection wherein the two pairs of cells do not detect simultaneously but can detect within a predetermined distance of one another.

When the first condition and one of the other three conditions are satisfied, a ribbon tear defect has been detected and the present invention will generate a reject signal to the inspection machine to remove the container from the inspection station and further processing. The circuit of the present invention also includes indicators and counters which respond to the signals generated by the circuitry to provide information during the inspection process. For example, a lamp and counter are provided for a visual indication during an inspection cycle and a total of the number of inspections completed. Lamps and counters also respond to a failure to rotate a container, the failure of one of the photovoltaic cells and the rejection of a container. Indicators are also provided for a visual indication for each of the combinations of conditions when they are satisfied, when a seam is detected and for each of the cells when they respond to a seam or a defect.

It is an object of the present invention to distinguish ribbon tear defects from seams and other defects in the side walls of a wide mouth glass container.

It is another object of the present invention to provide a means and a method for decreasing the cost and increasing the accuracy of the ribbon tear defect inspection process.

BRIEF DESCRIPTION OF THE DRAWINGS

FIG. 4 is a schematic diagram of one of the amplifiers of FIG. 1;

FIG. 5 is a schematic diagram of one of the comparators of FIG. 1;

FIGS. 9, 11 and 12 are schematic diagrams of the detector channel circuits of FIG. 1;

FIGS. 10A and 10B are wave form diagrams of various signals generated in the circuit of FIG. 9 for two sets of input signal conditions;

FIGS. 13A and 13B are wave form diagrams of various signals generated in the circuit of FIG. 12 for two sets of input signal conditions.

DESCRIPTION OF THE PREFERRED EMBODIMENT

Figure 1:
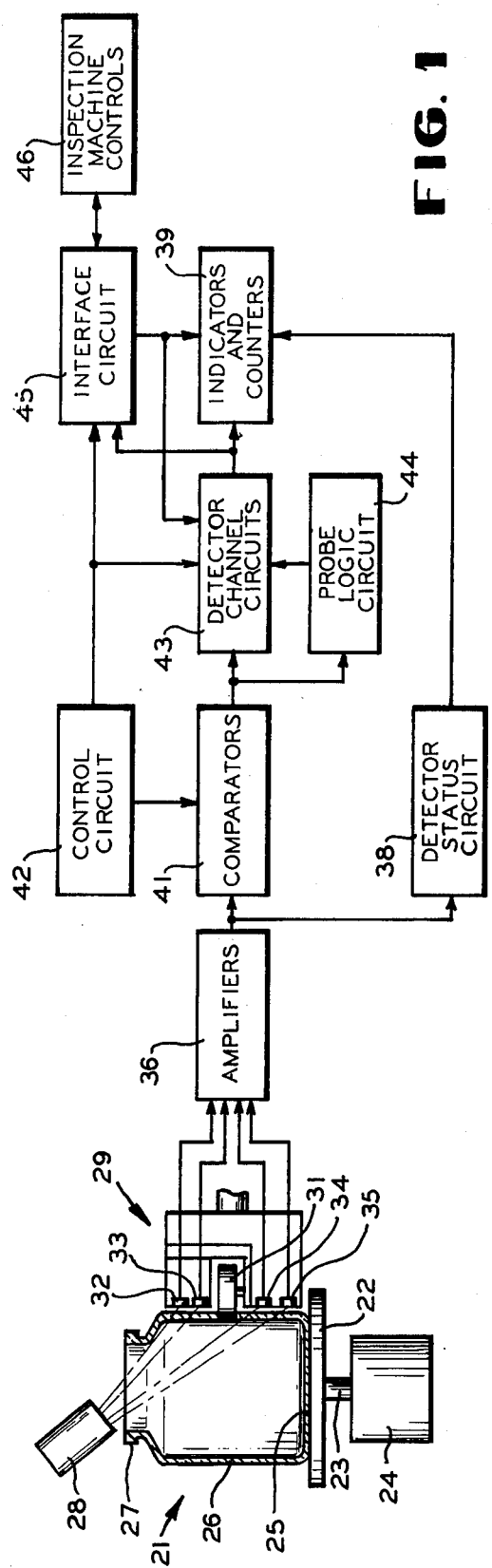
FIG. 1 is a partial schematic, partial block diagram of an apparatus for detecting defects in glass containers according to the present invention.

In FIG. 1, a glass container 21 is shown in cross-section mounted on a spinner pad 22. The pad 22 is connected to the output shaft 23 of a motor 24 for rotating the container 21 about its longitudinal or vertical axis. The container 21 is typically a wide-mouth glass bottle having a bottom 25 at a lower end and sides 26 which terminate at an upper end in an annular rim 27. The apparatus of the present invention can be utilized in cooperation with a glass container inspection machine such as that shown in U.S. Pat. No. 3,313,409. It is disclosed in that patent that glass containers are indexed one at a time through a rotary type inspection device which performs various inspections for attributes of the glass containers at a plurality of inspection stations. Most of these inspection stations require that the glass container be rotated and, therefore, the spinner pad 22, output shaft 23 and motor 24 are typical of similar devices disclosed in more detail in the cited patent.

A light source 28 is positioned above and to one side of the opening defined by the rim 27. The light source 28 is tilted from the vertical so as to illuminate the sides 26 of the glass container 21 from the inside thereof. A detector assembly 29 is fixedly mounted on the inspection machine (not shown) and includes a pair of rotatably mounted guide wheels 31 which contact the outside of the glass container 21 as it is rotated. The wheels 31 maintain a predetermined spacing between the sides 26 and four light responsive devices which typically can be photovoltaic cells commonly called solar cells or photodiodes. The light responsive devices are divided into two pairs, an upper pair comprising a top cell 32 and a bottom cell 33 and a lower pair comprising a top cell 34 and a bottom cell 35, the four cells being positioned along a vertical line adjacent the container side. The cells are responsive to the light which is transmitted through the walls of the container in the immediate vicinity of each of the cells. The amount of light reaching the cells is affected by defects and seams in the walls of the glass container.

Figure 3:
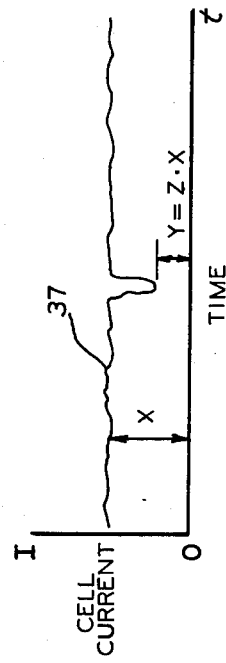
FIG. 3 is a wave form diagram of a typical light responsive cell output signal.
Figure 2:
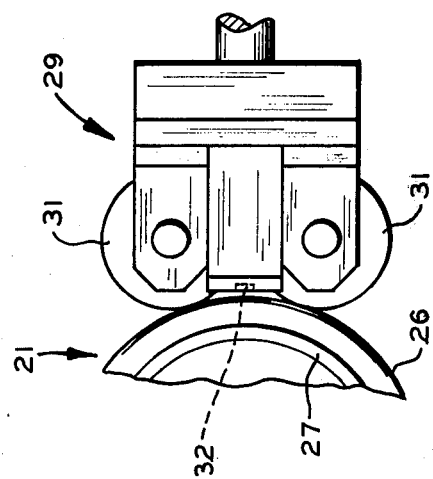
FIG. 2 is an enlarged, fragmentary plan view of the container and the detector assembly of FIG. 1.

Each cell is responsive to the received light to generate an electrical current having a magnitude proportional to the amount of light received. The output signals from the cells are the inputs to individual amplifiers 36. Each of the amplifiers 36 converts the input signal from its associated cell from a current proportional to a voltage proportional signal. There is shown in FIG. 3 a typical wave form associated with one of the cells plotted as cell current versus time. As the glass container 21 is rotated, the cell generates an output signal 37 which is basically a d. c. signal having a slight variation in magnitude X due to electrical noise and minor irregularities in the surface of the glass walls and the rotation thereof past the detector assembly 29. When a defect such as a bubble or a ribbon tear or a seam passes between the light source 28 and the cell, the amount of light reaching the cell is diminished and the cell output signal magnitude is decreased such as is shown by the current level Y in FIG. 3. Each amplifier 36 converts the current wave form 37 to a voltage wave form having a magnitude proportional to the amount of light received by the cell and amplifies the voltage wave form in logarithmic form.

The voltage proportional signal from each of the amplifiers, before the logarithm is taken, is the input to a detector status circuit 38 which detects the failure of one or more of the cells, the absence of a container or the absence of rotation of the container. When one of these conditions is detected, the circuit 38 generates an output signal to an indicators and counters circuit 39 to light a warning lamp. The circuit 39 also generates signals to counters in the circuit 39 to indicate the number of containers which have been present in the defect inspection station and the number of those containers which have been rotated.

The amplified signal from each of the amplifiers is an input to an associated one of a plurality of comparators 41. A filter removes the d. c. component of the signal to leave the Y component. A control circuit 42 generates a plurality of reference signals each of which is compared with each one of the Y component signals to generate detection signals to a plurality of detector channel circuits 43 and a probe logic circuit 44. The circuit 44 includes logic for recognizing an angled ribbon tear and generating a signal to the detector channel circuits 43 upon such a detection. The circuits 43 include logic for detecting various types of defects and generating signals to the indicators 39 for a visual identification of the defects. The circuits 43 also respond to the detection of a defect by sending a reject signal through an interface circuit 45 to an inspection machine controls circuit 46. The circuit 46 responds to the reject signal by removing the defective container from the inspection machine. The inteface circuit 45 also generates signals to the indicators and counters 39 to light a reject indicator and update a count of the rejected containers. The control circuit 42 provides information to the interface circuit 45 as to the speed of rotation and the body diameter of the container 21. The circuit 45 responds to this information by generating signals to enable the detector channel circuits 43 to distinguish between seams which are approximately 180° apart and ribbon tear defects which generate similar detection signals since a ribbon tear is generally less than 180° from the last detected seam.

The following is a brief explanation of the system of reference numerals and symbols utilized in the description of the preferred embodiment of the present invention as illustrated in FIGS. 4 through 14. The input leads to each circuit have been positioned at the left margin and the output leads have been positioned at the right margin. All output leads from a circuit have been designed with the general reference numeral for the circuit followed by a dash and a number such as an output lead 36-1 in FIG. 4. Therefore, each input lead to a circuit will be identified as to the circuit from which the input signal was generated. If the input lead is connected to a source external to the circuits of FIGS. 4–14, it will be designed with a reference numeral included in the sequence of reference numerals for the circuit in question. The input and output leads will also be identified with symbols representing the signals carried thereby as a further aid in understanding the illustrated circuits.

The schematics include many standard graphic symbols for individual circuit elements and integrated circuits. The operational amplifiers and integrated circuit logic elements are each identified by a reference numeral and each input or output thereof is identified by that reference numeral followed by a dash and a numeral such as an inverting input 53-1 of an operational amplifier 53 in FIG. 4. The logic elements operate at definable logic signal voltage levels such as a positive fifteen volts for logic true and a system ground potential for logic false. The logic true signal will be referred to as "1" and the logic false signal as "0".

Referring to FIG. 4, there is shown one of four similar amplifiers 36, one for each of the cell output signals. The cells are paired to reduce electrical noise from small defects which otherwise could significantly change the level of the cell output signal and cause a false detection. Thus, the cells 32 and 33 of FIG. 1 are paired and the cells 34 and 35 are paired. The amplifier 36 has a pair of input leads 51-1 and 51-2 which can be connected across any one of the cells. For example, the upper top solar cell 32 can be connected across the leads 51-1 and 51-2 to generate an input signal represented as a current flow having a magnitude proportional to the amount of light received by the cell 32. The leads 51-1 and 51-2 are connected to a pre-amplifier 52 which converts the solar cell signal from a current proportional to a voltage proportional signal.

The pre-amplifier 53 includes an operational amplifier 53 having an inverting 53-1, a non-inverting input 53-2 and an output 53-3. The maximum output voltage magnitude is limited by the supply voltages connected to a positive supply voltage input 53-4 and a negative supply voltage input 53-5. Typically, the positive and negative supply voltages are plus 15 and minus 15 volts respectively and are generated by a system power supply (not shown) connected to the supply voltage input leads. The amplifier 53 is frequency compensated externally with a capacitor 54 connected between a compensation input 53-6 and the input line 51-2 which in turn is connected to the system ground potential.

A capacitor 56 is connected to the line 51-1 and is connected to the line 51-2 to filter high frequency noise on the input signal. A pair of resistors 57 and 58 are connected in series between the input line 51-1 and the inverting input 53-1. The resistor 57 limits the input signal current flow to protect the cell 32 and the amplifier 53. A capacitor 59 is connected between the junction of the resistors 57 and 58 and the input line 51-2 wherein the resistor 57 and the capacitor 59 function as a filter for lower frequency noise. A resistor 61 is connected between the input 53-1 and the output 53-3 as a feedback resistor and the values of the resistors 58 and 61 determine the gain of the pre-amplifier. A capacitor 62 is connected in parallel with the resistor 61 to reduce the a. c. gain and a capacitor 63 is connected between the output 53-3 and the line 51-2 to filter the output signal generated at the output 53-3.

The current flow generated through the cell 32 from the line 51-1 to the line 51-2 is the input signal at the inverting input 53-1 and produces a potential difference between the inputs. The amplifier 53 amplifies this potential difference to generate an output voltage having a magnitude proportional to the amount of light received by the cell. This output signal is applied to a logarithmic amplifier 64 and an output lead 36-1. The signal is designated as the BT signal (the cells 32 and 33 being the "B" pair of which the cell 32 is the top "T") and the line 36-1 is connected to the detector status circuit 38 of FIG. 6. Similar amplifiers (not shown) generate BB ("B" pair, bottom "B" cell), AT ("A" pair, top "T" cell) and AB ("A" pair, bottom "B" cell) signals to the detector status circuit 37 on separate lines (not shown).

The amplifier 64 is utilized to eliminate differences in the magnitude of the output current among the cells for the same amount of received light. The output signal from the pre-amplifier 52 is viewed as a d. c. level times a percentage change from that d. c. level. Utilizing the wave form of FIG. 3 is an example, if the d. c. signal level is represented as X and the percentage change corresponding to a typical ribbon tear defect as Z, then the magnitude Y of the output signal for the defect can be represented by the equation $Y = Z \cdot X$. If we utilize the logarithmic amplifier to take the logarithem of the output signal Y, then $\log Y = \log Z \cdot X = \log Z + \log X$. If this signal is filtered to remove the d. c. component log X, the remaining a.c. signal is proportional to the percentage of the d. c. signal which the defect signal represents which will be the same for each of the cells for the same amount of received light.

The output lead 53-3 of the amplifier 53 is connected to an inverting input 65-1 of an operational amplifier 65 through a resistor 66. The amplifier 65 has a non-inverting input 65-2 connected to the line 51-2 and an output 65-3 connected to a resistor 67. A positive supply voltage input 65-4 and a negative supply voltage input 65-5 are connected to the system power supply (not shown). A pair of power supply filter capacitors 68 and 69 are connected between the leads 65-4 and 65-5 respectively and the line 51-2 to prevent high frequency oscillations due to power supply impedance. A relatively high frequency filter comprises a capacitor 71 and a resistor 72 connected in series between the inverting input 65-1 and the line 51-2.

The feedback circuit for the amplifier 65 includes a capacitor 73 connected between the inverting input 65-1 and the output 65-3 to reduce the a. c. gain. A NPN transistor 74, a diode 75, a resistor 76 and a capacitor 77 are all connected in parallel between the inverting input 65-1 and the end of the resistor 67 opposite the end connected to the output 65-3. The transistor 74 has a collector and a base connected together at the input 65-1 and an emitter connected to the resistor 67 to function as a feedback diode. The transistor 74 is the nonlinear feedback element required in the feedback circuit for logarithmic operation. The diode 75 has a cathode connected to the input 65-1 and an anode connected to the resistor 67. The diode 75 prevents saturation of the amplifier should the input offset voltages tend to drive the amplifier into generating a positive potential output signal when the signal on the input 65-1 is at or near the system ground potential. The resistor 76 is a feedback resistor such that the values of the resistors 66 and 76 determine the gain of the amplifier. The value of the resistor 67 is typically much less than the value of the resistor 76 so that it does not significantly contribute to determining the gain. The capacitor 77 functions as a filter for high frequency noise.

The output signal from the logarithmic amplifier 64 is the input to a relatively high gain amplifier 78. The resistor 67 is connected to an inverting input 79-1 of an operational amplifier 79 through a pair of series connected resistors 81 and 82. The amplifier 79 has a non-inverting input 79-2 connected to the line 51-2; an output 79-3, a positive power supply input 79-4 connected to the positive potential system power supply (not shown) and a negative power supply input 79-5 connected to the negative potential system power supply (not shown). A pair of power supply filter capacitors 83 and 84 are connected between the line 51-2 and the inputs 79-4 and 79-5 respectively. A capacitor 85 is connected between the line 51-2 and the junction of the resistors 81 and 82 such that the capacitor 85 and the resistor 81 function as a low pass filter.

A resistor 86 and a thermistor 87 are connected in series between the input 79-1 and the output 79-3 as a feedback circuit. The values of the resistors 82 and 86 and the thermistor 87 determine the gain of the amplifier 78. The thermistor is provided to temperature compensate the output signal from the amplifier 78 for the temperature dependent characteristics of the transistor 74 in the logarithmic amplifier 64. A capacitor 88 is connected between the input 79-1 and the output to reduce the a. c. gain. A pair of resistors 89 and 91 are connected in series between the output 79-3 and an amplifier output line 36-2. A capacitor 92 is connected between the line 51-2 and the junction of the resistors 89 and 91 such that the capacitor and the resistors function as a low pass "T" type filter for the output signal LBT representing the logarithm of the signal BT.

There is a diode drop associated with the transistor 74 which must be compensated by offsetting the input signal to the amplifier 79. A NPN transistor 93 has a collector and a base connected to the positive potential system power supply (not shown) through a resistor 94. An emitter of the transistor 93 is connected to the line 51-2 such that a diode voltage drop is generated across the transistor. If the transistors 74 and 93 are formed on the same substrates, such as an integrated circuit chip, their diode drops will be identical. The collector and base of the transistor 93 are connected to the input 79-1 through a pair of resistors 95 and 96 connected in series. A capacitor 97 is connected between the line 51-2 and the junction of the resistors 95 and 96 such that the capacitor and the resistors function as a low pass "T" type filter to couple the diode drop offset voltage to the inverting input 79-1. The input 79-1 is also connected to the negative potential system power supply through a relatively large value resistor 98 to provide a reference level for the offset voltage.

In summary, the amplifier 36 represents one of four similar amplifiers each receiving an input signal from a light responsive device such as a photovoltaic cell. As shown in FIG. 3, the cell 32 generates a current having a magnitude proportional to the amount of received light. A preamplifier 52 converts the input current into a voltage wave form having a magnitude proportional to the amount of light received by the cell. A logarithmic amplifier takes the logarithm of the voltage wave form to enable the wave form to be separated into its d. c. component and an a. c. component representing a detected defect measured as a percentage of the d. c. component. The output signal from the logarithmic amplifier is then amplified and applied to the comparators 51. The wave form LBT on the line 36-2 is of the same general shape as the wave form of FIG. 3, but has undergone three inversions by the operational amplifiers and a logarithmic operation. Therefore, the wave form LBT is positive going with respect to the system ground potential with the magnitude in proportion to the log of the percentage of the d. c. signal level representing the amount of light reaching the photovoltaic cell.

There is shown in FIG. 5, one of four similar comparator circuits 41 and an associated portion of the control circuit 42. For purposes of illustration, the comparator circuit for the signal LBT is described. The line 36-2 is connected to an input of each of four operational amplifiers which function as comparators to compare the LBT signal magnitude with each of four reference levels to generate detection signals to the detector channel circuits 43. The line 36-2 is connected to the system ground potential through a series connected resistor 101 and capacitor 102 comprising a low pass filter. The junction of the resistor 101 and the capacitor 102 is connected to an inverting input 103-1 of an operational amplifier 103 through a coupling capacitor 104. A resistor 105 is connected between the input 103-1 and the system ground potential so that the capacitor 104 and the resistor 105 function as a high pass filter to remove the log X d. c. component of the input signal. Therefore, only the log Z component is compared with the reference signals to eliminate mismatches in the light detection cells.

The amplifier 103 has a non-inverting input 103-2 connected to receive a reference signal from the control circuit 42, an output 103-3 and a positive power supply input 103-4 and a negative power supply input 103-5 connected to the positive potential system power supply (not shown) and negative potential system power supply (not shown) respectively. The output 103-3 is connected to the positive potential system power supply through a resistor 106 to supply current to drive the following circuits at a definable logic level since the amplifier is a relatively low output current device. The output 103-3 is connected to an output line 41-1 through a current limiting resistor 107.

The control circuit 42 generates four reference signals designated 0−, I−, II + II− on a plurality of output lines 42-1, 42-2, 42-3 and 42-4 respectively. The line 42-1 is connected to a tap of a potentiometer 108 connected in series with a resistor 109 between the negative potential system power supply (not shown) and the system ground potential. The tap is adjusted to generate a relatively large negative potential reference voltage designated 0−. The line 42-1 is connected to the input 103-2 through a resistor 111 and a capacitor 112 is connected between the input 103-2 and the system ground potential. The resistor 111 and the capacitor 112 function as a low pass filter for the reference signal.

When the LBT signal is a. c. coupled, the leading edge of the log Z component will generate a negative going pulse wave form and the trailing edge will generate a positive going pulse wave form, each with a magnitude proportional to the amount of the reduction in the received light and therefore proportional to the severity of the defect.

When there is no defect present or the detected defect is less than severe, the signal at the input 103-1 will have a magnitude between the system ground potential and the 0− signal level. Since the input signals are not applied through current limiting input resistors, the amplifiers will tend to saturate for relatively small differences in the input signals. The amplifier 103 will generate an output signal having a magnitude of the negative potential system power supply voltage. Thus, the output signal BTO− on the line will be below the system ground potential to generate a logic "0" representing the absence of a severe defect. When the negative going signal at the input 103-1 exceeds the 0− signal level, the amplifier 103 will saturate and generate the positive potential system power supply voltage. The line 41-1 will then be at logic "1" representing the presence of a severe defect. When the signal at the input 103-1 returns to the system ground potential, the output signal will return to "1" and the positive going signal will not cause a change in the "1" signal on the line 41-1.

The comparator 41 includes an output line 41-2 on which there is generated a signal representing the detection of an average or normal size defect. An operational amplifier 113 has an inverting input 113-1, a non-inverting input 113-2 connected to the junction of the capacitor 104 and the resistor 105 to receive the log Z component of the LBT signal and an output 113-3 connected to the line 41-2 through a resistor 114. The power supply inputs to the amplifier 113 are connected in a manner similar to those of the amplifier 103 and are not shown. The output 113-3 is also connected to the positive potential system power supply (not shown) through a resistor 115 to drive the following circuits.

The control circuit 42 has the line 42-2 connected to a tap of a potentiometer 116 connected in series with a resistor 117 between the negative potential system power supply (not shown) and the system ground potential. The tap is adjusted to generate a normal or average potential reference voltage designated I− having a magnitude between the system ground potential and the magnitude of the 0− reference voltage. The line 42-2 is connected to the input 113-1 through a resistor 118 and a capacitor 119 is connected between the input 113-1 and the system ground potential. The resistor 118 and the capacitor 119 function as a low pass filter for the reference signal. When there is no defect present or the defect is less than a normal one, the signal at the input 113-2 will have a magnitude between the system ground potential and the I− signal level. The amplifier 113 will generate an output signal having a magnitude of the positive potential system power supply voltage to generate a logic "1" on the BTI- line 41-2 representing the absence of a normal defect. When the detected defect is normal to severe, the negative going signal will exceed the I− signal and the "0" signal will be generated representing the presence of a normal to severe defect.

The comparator 41 also includes an output line 41-2 on which there is generated a signal representing the detection of small defect which is of the type to focus the light on the cell actually increasing the amount of received light. Such a defect will generate a positive going signal LBT on the line 36-2. An operational amplifier 121 has an inverting input 121-1 connected to the junction of the capacitor 104 and the resistor 105 to receive the log Z component of the LBT signal, a non-inverting input 121-2 connected to the reference signal line 42-3 and an output 121-3 connected to the line 41-3 through a resistor 122. The power supply inputs to the amplifier 121 are connected in a manner similar to those of the amplifier 103 and are not shown. The output 121-3 is also connected to the positive potential system power supply (not shown) through a resistor 123 to drive the following circuits.

The control circuit 42 has the line 42-3 connected to a tap of a potentiometer 124 connected in series with a resistor 125 between the positive potential system power supply (not shown) and the system ground potential. The tap is adjusted to generate a small potential reference voltage designated II+ having a relatively small positive magnitude. The line 42-3 is connected to the input 121-2 through a resistor 126 and a capacitor 127 is connected between the input 121-2 and the system ground potential. The resistor 126 and the capacitor 127 function as a low pass filter for the reference voltage. When there is no defect present, the input 121-1 will be at the system ground potential and the amplifier will generate an output signal having the magnitude of the positive potential system power supply voltage to generate a logic "1" on the line 41-3 representing the absence of a focusing type defect. If a focusing type defect occurs, the leading edge will generate a positive going pulse wave form which exceeds the reference voltage in magnitude and the amplifier will generate a "0" on the line 41-3. The amplifier 121 will also respond to the positive going wave form generated by the trailing edge of the light reducing type defects to generate a "0" output signal.

The comparator includes an output line 41-4 on which there is generated a signal representing the detection of a small defect of the light reducing type. An operational amplifier 128 has an inverting input 128-1 connected to the reference signal line 42-4, a non-inverting input 128-2 connected to the junction of the capacitor 104 and the resistor 105 to receive the log Z component of the LBT signal and an output 128-3 connected to the line 41-4 through a resistor 129. The power supply inputs to the amplifier 128 are connected in a manner similar to those of the amplifier 103 and are not shown. The output 128-3 is also connected to the positive potential system power supply (not shown) through a resistor 131 to drive the following circuits.

The control circuit has the line 42-4 connected to a tap of a potentiometer 132 connected in series with a resistor 133 between the negative potential system power supply (not shown) and the system ground potential. The tap is adjusted to generate a small potential reference voltage designated II− having a relatively small negative magnitude. The line 42-4 is connected to the input 128-1 through a resistor 134 and a capacitor 135 is connected between the input 128-1 and the system ground potential. The resistor 134 and the capacitor 135 function as a low pass filter for the reference voltage. When there is no defect present or it is less than a small defect, the signal at the input 128-2 will have a magnitude between a small negative potential and the II+ level. The amplifier 128 will generate an output signal having a magnitude of the positive potential system power supply voltage to generate a logic "1" on the BTII- line 41-4 representing the absence of a small defect. When the detected defect is of the light reducing type, the "0" signal will be generated on the line 41-4 in response to the negative going wave form at the input 128-2. A "0" will also be generated by the negative going wave form generated by the trailing edge of a focusing type defect.

A diode 136 has an anode connected to the output 121-3 and a cathode connected to the output 128-3. Therefore, when a small to severe defect is detected and the amplifier 128-3 generates an output signal having a magnitude of the negative potential system power supply voltage, the junction of the resistors 122 and 123 will be pulled negative also generating a logic "0" on the line 41-3. Thus, a logic "0" on the line 41-3 represents the detection of small to severe defect of either type and the logic signal is designated as BTII+−.

In summary, the comparator 71 filters the d. c. component from the output signal of the amplifier 36 and compares any remaining a. c. signal representing a defect with each of four reference signal levels to detect defects of varying severity and types. The comparator circuit shown in FIG. 5 compares the a. c. component of the signal LBT from the top "B" cell with the four reference levels 0−, I−, II+ and II− to generate the logic signals BT0−, BTI−, BTII+− and BTII−. Three similar circuits (not shown) compare the a. c. components of the signals from the other cells with the same reference signals to generate similar logic signals. These logic signals are utilized in the detector channel circuits 43 to determine if the container should be rejected and to detect various operations and faults in the system.

The inspection machine with which the present invention is associated generates several signals which are utilized in the logic circuitry for detecting ribbon tear defects. One such signal, the bottle present signal BP, is associated with the input lines 38-1 and 38-2 and 38-3 of the detector status circuit 38 shown in FIG. 6. As long as there is a container loaded into the inspection station, the BP signal is generated to enable a flip flop. If a GUAGE signal is generated in the interface circuit 45 on a line 45-6 (the GUAGE signal is generated in response to an inspection machine signal representing that the container is being inspected as will be discussed in connection with FIG. 11), the flip flop will be set to ground a TOTAL INSPECTION output line 38-4 to light an indicator lamp and trip a counter. The logarithmic output signals from each of the amplifiers are the inputs to a. c. filters and comparators for detecting the log Z components representing seams and ribbon tears. If no log Z components are received indicating the absence of a container or no rotation thereof, a second flip flop is set. If no bottle is present or no rotation occurs, the output signals from the two flip flops ground a NO ROTATION line 38-5 to light an indicator lamp and trip a counter. The pre-amplifier output signals from each of the amplifiers are the inputs to comparators for detecting a failed cell. If no pre-amplified signal is received for one or more cells, a third flip flop is set to ground a DARK CELL line 38-6 to light an indicator and trip a counter.

Figure 6:
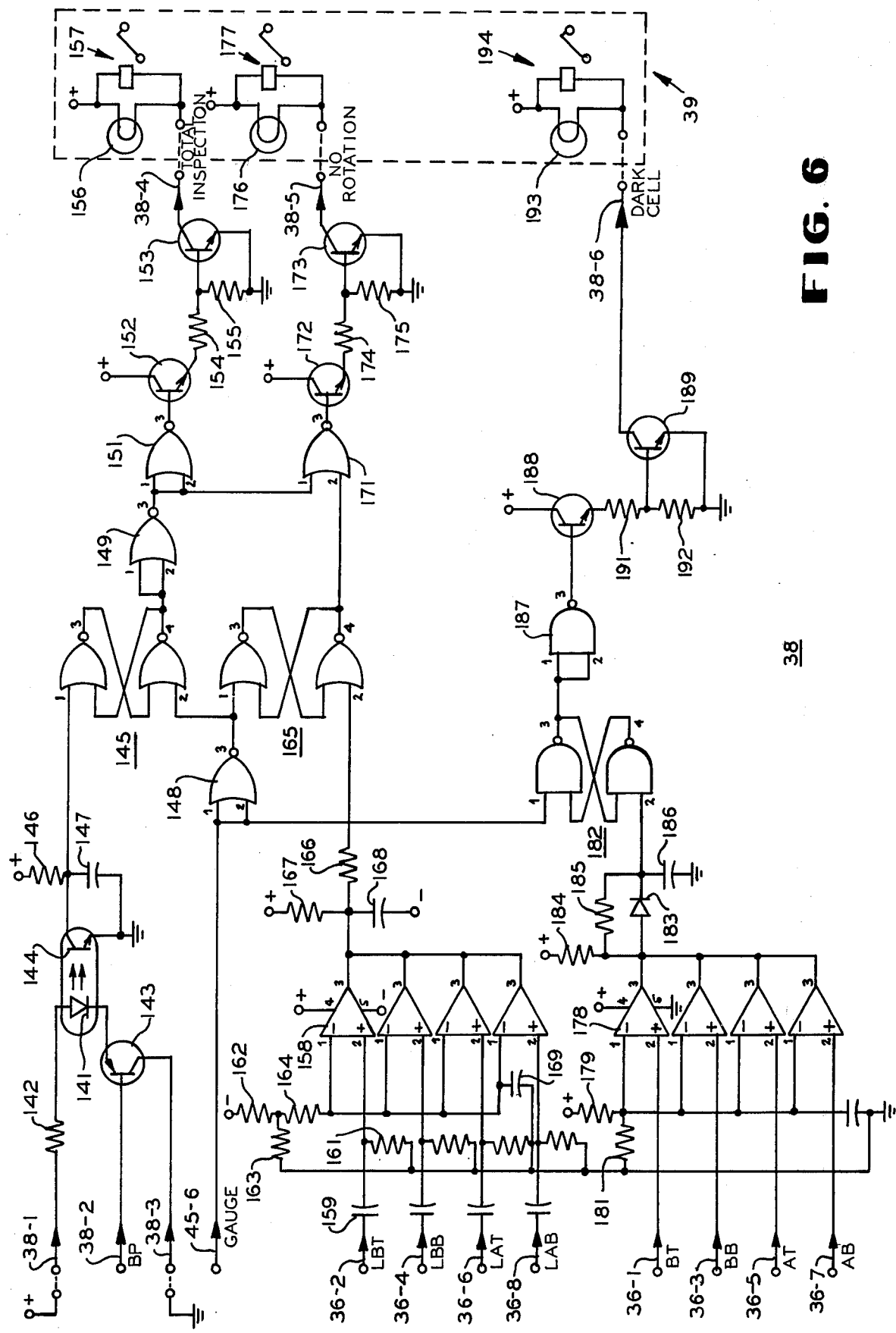
FIG. 6 is a schematic diagram of the detector status circuit of FIG. 1.

There is shown in FIG. 6, the input line 38-1 connected to an external positive potential power supply (not shown), the input line 38-2 which receives the BP signal from an external detector (not shown) and the input line 38-3 connected to an external ground potential source (not shown). The line 38-1 is connected to an anode of a photoemissive diode 141 through a current limiting resistor 142. The diode has a cathode connected to an emitter of a PNP transistor 143 which in turn has a base connected to the line 38-2 and a collector connected to the line 38-3. If no container is present, the BP signal will be at the system ground potential to turn on the transistor 143 to provide current flow through the diode 141. A phototransistor 144 is responsive to the light output of the diode 141 and has a collector connected to an input 145-1 of a NOR flip flop 145 and an emitter connected to the system ground potential. The photoemissive diode 141 and the phototransistor 144 isolate the inspection machine circuits from the detector status circuit 38 to reduce electrical noise. The input 145-1 is connected to the positive potential system power supply (not shown) through a resistor 146 and to the system ground potential through a capacitor 147. As long as no container is present, the phototransistor 144 will maintain the capacitor 147 discharged and place a "0" at the input 145-1.

The GUAGE signal line 45-6 is connected to both inputs of a NOR element 148 which functions as a signal inverter. An output 148-3 of the NOR 148 is connected to an input 145-2 of the NOR flip flop 145. The NOR flip flop 145 will generate a "0" at a pair of outputs 145-3 and 145-4 when both inputs are at "1", will generate the signals at the inputs 145-2 and 145-1 at the outputs 145-3 and 145-4 respectively when one input is at "1" and the other is at "0" and will not change the output signals when both input signals go to "0". Before a bottle is loaded into the ribbon tear inspection station, the BP signal will be at the system ground potential level to turn on the transistor 143 thereby permitting current flow in the diode 141 and turning on the phototransistor 144. The capacitor 147 will be discharged to the system ground potential level to generate a logic "0" at the input 145-1. The GUAGE signal on the line 45-6 will be a "0" and the NOR 148 will generate a "1" at the input 145-2 to reset the NOR flip flop to generate a "0" at the output 145-4.

The output 145-4 is connected to both inputs of a NOR 149 which functions as an inverter. The NOR 149 has an output 149-3 which is connected to both inputs of a NOR 151 which also functions as an inverter. The NOR 151 has an output 151-3 connected to a base of a NPN transistor 152 having a collector connected to the positive potential system power supply (not shown) and an emitter connected to the base of a NPN transistor 153 through a resistor 154. The transistor 153 has a collector connected to the line 38-4 and an emitter connected to the system ground potential and the base is connected to the system ground potential through a resistor 155. The "0" at the output 145-4 is inverted twice to ground the base of the transistor 152 thereby turning it off. The base of the transistor 153 is also at the system ground potential to turn off the transistor 153. The line 38-4 is connected to an external positive potential power supply (not shown) through an incandescent lamp 156 and a coil of an electromagnetically operated counter 157. Since the transistor 153 is turned off, there will be no current flow through the lamp or the counter.

If a container is loaded into the ribbon tear inspection station, the BP signal will switch to the positive potential of the external power supply to turn off the transistors 143 and 144. The capacitor 147 will charge to the positive potential system power supply voltage to generate a "1" at the input 145-1 to enable the flip flop. The GUAGE signal will change to a logic "1" during the inspection operation to generate a "0" at the input 145-2. The flip flop is set by the "0" to generate a "1" at the output 145-4 which is inverted twice to turn on the transistor 152 which in turn provides a bias voltage to turn on the transistor 153 and connect the line 38-4 to the system ground potential. Current now flows to turn on the TOTAL INSPECTION indicator lamp 156 and cycle the counter 157 which accumulates a count of the total number of containers inspected. When the inspection is complete, the GUAGE signal will return to "0" to reset the flip flop output 145-4 to "0" and turn off the lamp 156. If the BP signal is not generated because a container was not loaded, the "0" at the input 145-1 will disable the flip flop 145 so that the GUAGE = "1" signal cannot set it and turn on the lamp 156.

The LBT line 6-2 is connected to a non-inverting input 158-2 of an operational amplifier 158 through a capacitor 159. A resistor 161 is connected between the input 158-2 and the system ground potential wherein the capacitor 159 and the resistor 161 function as a high pass filter to remove the d. c. component of the LBT signal and apply the log Z component to the amplifier. A pair of resistors 162 and 163 are connected in series between the negative potential system power supply (not shown) and the system ground potential to generate a reference voltage. An inverting input 158-1 is connected to the junction of the resistors 162 and 163 through a current limiting resistor 164. A positive potential power supply input 158-4 and a negative potential power supply input 158-5 are connected to the positive and negative potential system power supplies (not shown) respectively. An output 158-3 is connected to an input 165-2 of a NOR flip flop 165 through a current limiting resistor 166. The output 158-3 is also connected to the positive potential system power supply (not shown) through a resistor 167 and to the negative potential system power supply (not shown) through a capacitor 168.

The lines 36-4, 36-6 and 36-8 from the other three amplifiers (not shown) are also connected through high pass filters to non-inverting inputs of operational amplifiers similar to the amplifier 158. Each inverting input of the four amplifiers is connected to the resistor 164 and to the system ground potential through a capacitor 169 to receive the reference voltage generated at the junction of the resistors 162, 163 and 164. The outputs of the amplifiers are connected together. When a container is present and rotating, each of the four input signals from the amplifiers has a log Z component to generate a negative potential pulse signal at the non-inverting inputs which is greater in magnitude than the negative potential reference signal at the inverting inputs. Therefore, the amplifiers will generate the negative potential system power supply voltage to charge the capacitor 168 thereto and place a "0" at the input 165-2 of the NOR flip flop 165. When the GUAGE signal goes to "0" before an inspection of a container, the NOR 148 will generate a "1" at an input 165-1 which is connected to the output 148-3. The NOR flip flop 165 will be reset to generate a "1" at the output 165-4 which is connected to an input 171-1 of a NOR 171. The NOR will generate a "1" if both inputs are at "0" and will generate a "0" for any other combination of input signals. The NOR 171 has an output 171-3 connected to a base of a NPN transistor 172 having a collector connected to the positive potential system power supply (not shown). An emitter of the transistor 172 is connected to a base of a NPN transistor 173 through a resistor 174. The transistor 173 has a collector connected to the line 38-5 and an emitter connected to the system ground potential and the base is connected to the system ground potential through a resistor 175. The NOR 171 generates a "0" to turn off the transistors 172 and 173. The line 38-4 is connected to an external positive potential power supply (not shown) through an incandescent lamp 176 and a coil of an electromagnetically operated counter 177. Since the transistor 173 is turned off, there will be no current flow through the lamp or the counter.

When a container is not present or there is no rotation, the log Z components will not be generated and the non-inverting inputs will be at the system ground potential. The amplifiers will then generate the positive potential system power supply voltage to charge the capacitor 168 through the resistor 167 to place a "1" at the input 165-2. The flip flop 165 is set by the "1" generate a "0" at the output 165-4 which is applied to the input 171-2 to enable the NOR 171. If there is no container present, a "1" will be generated by the NOR 149 at the output 149-3 which is connected to an input 171-1 of the NOR 171. The NOR 171 will continue to generate a "0" to maintain the lamp 176 in the off state. If a container is present, the NOR 144 will generate a "0" when the GUAGE signal goes to "1". Since both inputs are at "0", the NOR 171 will generate a "1" to turn on the transistors 172 and 173. Current now flows to turn on the NO ROTATION indicator lamp 176 and cycle the counter 177 which accumulates a count of the total number of containers not rotated.

The BT line 36-1 is connected to a non-inverting input 178-2 of an operational amplifier 178. A pair of resistors 179 and 181 are connected in series between the positive potential system power supply (not shown) and the system ground potential to generate a reference voltage at the junction of the two resistors which junction is connected to an inverting input 178-1. A positive potential power supply input 178-4 and a negative potential power supply input 178-5 are connected to the positive potential system power supply (not shown) and the system ground potential respectively. An output 178-3 is connected to an input 182-2 of a NAND flip flop 182 through a diode 183. The output 178-3 is connected to an anode of the diode 183 and to the positive potential system power supply (not shown) through a resistor 184. A resistor 185 is connected between the anode and a cathode of the diode 183 which has the cathode connected to the input 182-2. The input 182-2 is also connected to the system ground potential through a capacitor 186.

The lines 36-3, 36-5 and 36-7 from the other amplifiers (not shown) are also connected to non-inverting inputs of operational amplifiers similar to the amplifiers 178. Each inverting input of the four amplifiers is connected to the junction of the resistors 179 and 181 to receive the positive potential reference voltage and to the system ground potential through a capacitor 187 which is charged to the reference voltage level. The amplifier outputs are also connected together and the positive and negative power supply inputs (not shown) are connected in a manner similar to those of the amplifier 178.

An input 182-1 of the flip flop 182 is connected to the line 45-6 to receive the GUAGE signal. An output 182-3 is connected to a pair of inputs 187-1 and 187-2 of a NAND 187 which functions as an inverter. An output 187-3 is connected to a base of a NPN transistor 188 having a collector connected to the positive potential system power supply (not shown). An emitter of the transistor 188 is connected to a base of a NPN transistor 189 through a resistor 191. The transistor has a collector connected to the DARK CELL line 38-6 and an emitter connected to the system ground potential and the base is connected to the system ground potential through a resistor 192.

When the cells are receiving light, the average d. c. signal level on the input lines 36-1, 36-3 and 36-7 will exceed the positive potential reference voltage level and the amplifiers will generate the positive potential system power supply voltage at the outputs to forward bias the diode 183 and charge the capacitor 186 through the resistors 184 and 185 to apply a "1" at the input 182-2. When the GUAGE signal goes to "0" before an inspection of a container, the NAND flip flop 182 will be reset to generate a "1" at the output 182-3. The NAND 187 will invert the "1" to turn off the transistors 188 and 189 thereby preventing current flow through the lamp or the counter. The NOR 187 will continue to generate the "0" as the containers are inspected to maintain the lamp 193 in the off state.

When one or more of the cells goes dark, i.e. the cell fails or a defect blocks the light, the signal level on the corresponding input line will fall below the reference voltage level and the amplifier output will switch to the system ground potential. The diode 183 is reverse biased and the capacitor 186 will begin to discharge through the resistor 185. The values of the resistor 186 and the capacitor 186 are selected to provide a sufficiently long time constant so that if the cell went dark because a defect blocked the light, the capacitor will not discharge below the "1" logic level before the cell again generates a signal of a positive potential magnitude sufficient to switch the amplifier output back to the positive potential system supply level. When the cell goes dark due to a failure, the capacitor will discharge to the "0" logic signal level and the NAND flip flop 182 will be set to generate a "0" at the output 182-3 when the GUAGE = "1" signal is generated. The NAND 187 changes the "0" to a "1" to turn on the transistors 188 and 189. Current now flows to turn on the DARK CELL indicator lamp 193 and to cycle the counter 194 which accumulates a count of the total number of cell failures.

In summary, the detector status circuit 38 receives the bottle presence signal BP and derives the GUAGE signal from an external source at the ribbon tear inspection station. If a container is present, the GUAGE = "1" signal is generated during the inspection cycle to light a TOTAL INSPECTION indicator and cycle a counter of the number of inspections. The logarithmic output signals from each of the amplifiers 36 are monitored for the log Z components to detect the absence of rotation when a container is present. Such a failure will light a NO ROTATION lamp and cycle a counter of the number of no rotation failures. The circuit 38 also receives the pre-amplified cell output signals to detect the failure of one or more of the cells. The loss of the output signal from one or more of the cells for a predetermined length of time is indicated by lighting the DARK CELL lamp 193 and cycling the counter 194.

The circuits of FIGS. 7 through 14 include logic which utilizes the signals generated by the comparators 41 to determine if a ribbon tear defect has been detected by the cells. There are several conditions and combinations thereof which are considered. The following conditions have been selected as representing those most effective in detecting ribbon tear defects:

1. A or B where A and B represent a detection signal of a least a normal defect by the "A" and "B" pairs of cells respectively.
2. Signal repeats within 150° since seams are always approximately 180° apart.
3. Signal is greater in width than approximately 0.2 inch since seams are always narrower than that.
4. A* and B* do not occur simultaneously where A* and B* represent a detection signal of a short defect or a defect which is skewed or angled from the vertical by the "A" and "B" pairs of cells respectively.

The logic circuitry determines that a container should be rejected when the comparator output signals confirm that condition one plus conditions two or three or four are satisfied. The circuit shown in FIG. 7 is the probe logic circuit 44 which developes some of the signals utilized to determine if conditions one and four are satisfied.

Figure 7:
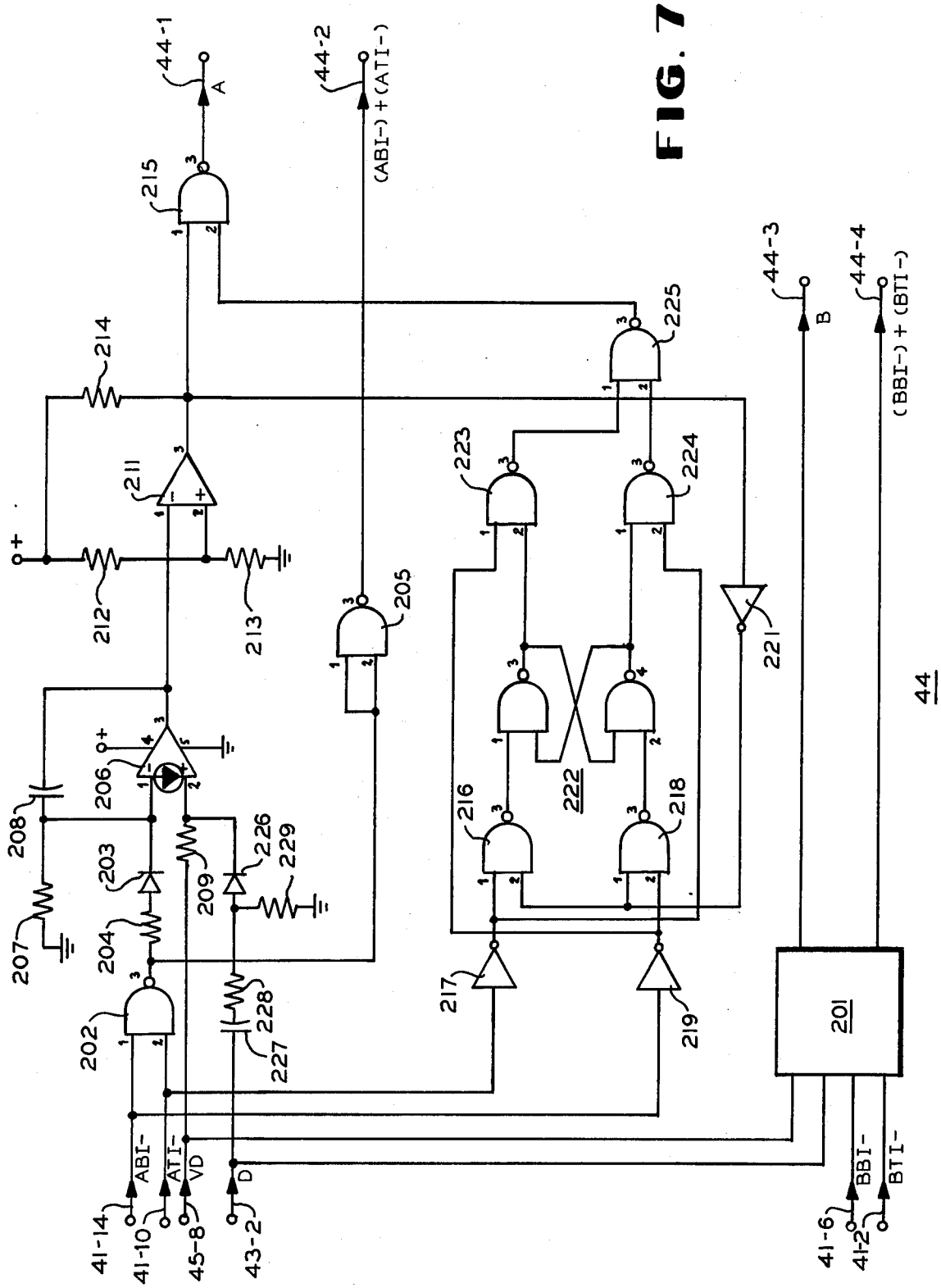
FIG. 7 is a schematic diagram of the probe logic circuit of FIG. 1.
Figure 8:
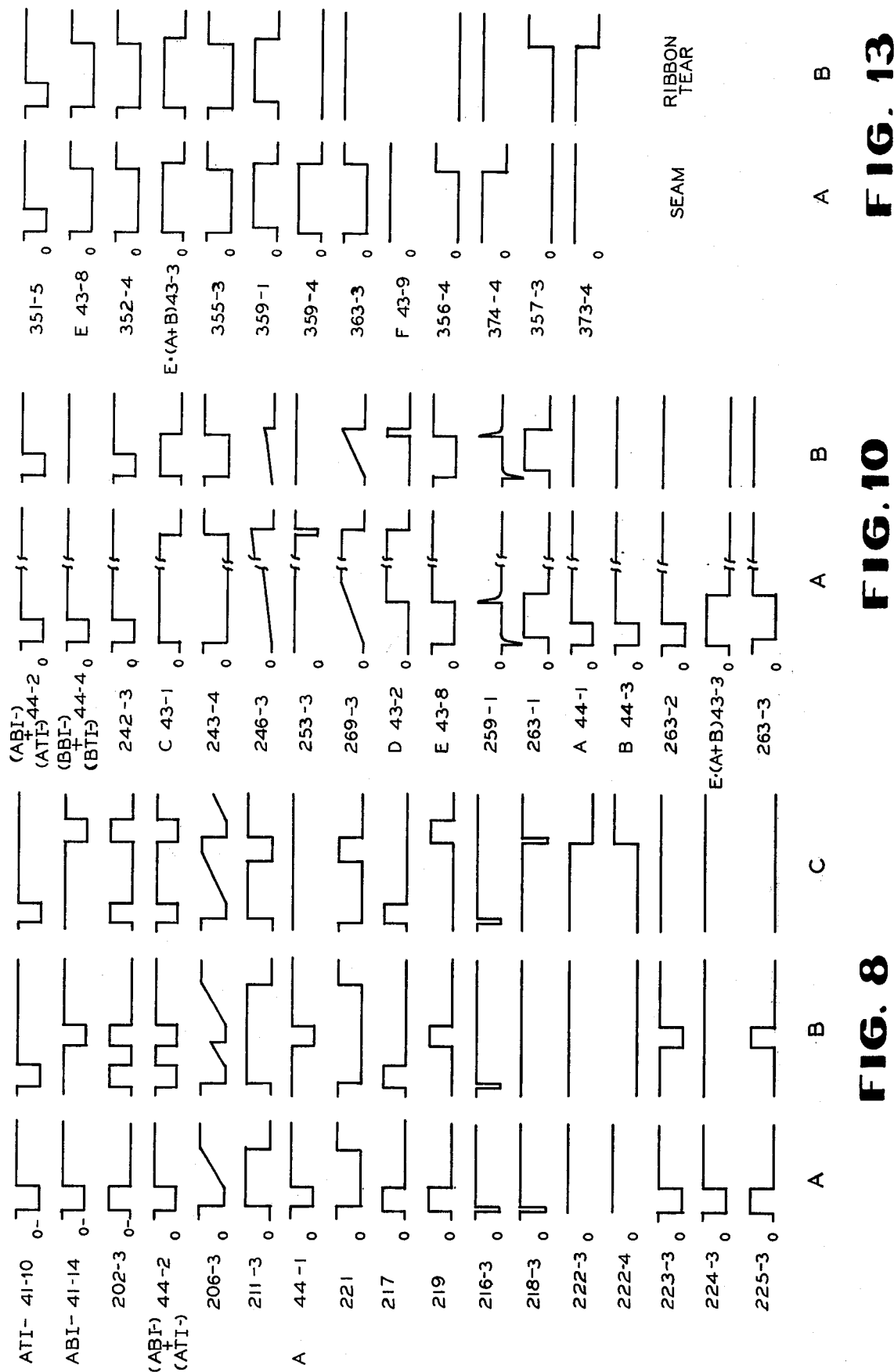
FIGS. 8A through 8C are wave form diagrams of various signals generated in the circuit of FIG. 7 for three sets of input signal conditions.

There is shown in FIG. 7, the probe logic circuit 44 for generating the A and B signals for condition one and signals representing the detection of a normal defect for conditions two and three. The normal level signals BTI−, BBI−, ATI− and ABI− on the lines 41-2, 41-6, 41-10 and 41-14 respectively are the inputs to the probe logic circuit 44. Only that portion of the probe logic utilizing the signals from the "A" pair of cells will be described in detail as the "B" logic portion is similar and is represented by a block 201. The ABI− line 41-14 is connected to an input 202-1 and the ATI− line 41-10 is connected to an input 202-2 of a NAND logic element 202. The NAND will generate a "0" if both inputs are at "1" and will generate a "1" for any other combination of input signals. An output 202-3 is connected to an anode of a diode 203 through a resistor 204 and to a pair of inputs 205-1 and 205-2 of a NAND 205 which functions as an inverter. The NAND 205 has an output 205-3 which is connected to a line 44-2 to generate a signal (ABI−) + (ATI−) representing the logic AND of the input signals to the NAND 202 where a "0" is generated by the detection of a defect or seam by either or both of the "A" cells.

The output from the NAND 202 is also the input to an operational amplifier for generating a signal A representing the detection of a defect skewed or angled from the vertical by less than a predetermined horizontal distance between the top and bottom cells of a pair. The amplifier is connected as an integrator wherein the charge on the integrating capacitor is reversed with a relatively fast time constant when a first one of the cells detects a defect and the charge is returned to the original polarity with a relatively slow time constant when the defect has passed the first cell. The slow time constant is selected so that the delay represents a horizontal distance on the outside of the container, typically three-eights of an inch. If the second cell of the pair detects the defect before the charge is returned to the original polarity, the A signal will be generated to indicate a ribbon tear defect. The circuit 201 utilizes the BBI− and BTI− signals to generate a B signal and a (BBI−) + (BTI−) signal in a similar manner.

There are shown in FIGS. 8A through 8C wave form diagrams for various signals generated by the circuit of FIG. 7 for three sets of input signal conditions. Each signal is identified as to the line or output lead on which it appears or the circuit element which generates it.

FIGS. 8A through 8C can be referenced as an aid in understanding the following discussion of the operation of the circuit of FIG. 7.

The amplifier 206 and the other amplifiers in the following FIGS. are commonly known as "Norton" amplifiers and are available from the National Semiconductor Corp., 2900 Semiconductor Drive, Santa Clara, California 95051 under part number LM1900. This dual input, internally compensated amplifier is designated to operate from a single power supply and to provide a large output voltage swing. If the inverting input is connected to the output by a capacitor and a positive potential reference voltage is applied to the non-inverting input, a change of signal at the inverting input from "1" to "0" will generate a sawtooth output wave form limited by the positive potential power supply voltage and terminated by a return to "1" at the inverting input.

The diode 203 has a cathode connected to an inverting input 206-1 of a "Norton" operational amplifier 206. The diode 203 compensates for an internal diode drop between the two inputs. The input 206-1 is connected to the system ground potential through a resistor 207 and to an output 206-3 through a capacitor 208. A non-inverting input 206-2 is connected to a line 45-8 through a resistor 209 to receive a signal VD which is proportional to the diameter and speed of the container being rotated. The values of the resistors 207 and 209 are approximately equal to generate the same bias at both inputs. A positive power supply input 206-4 is connected to the positive potential system power supply (not shown) and a negative power supply input 206-5 is connected to the system ground potential. Before a defect is detected, the ABI— and ATI— signals will be at "1" to generate a "0" at the output 202-3. The amplifier 206 will charge the capacitor 208 to the positive potential system power supply voltage with reference to the system ground potential applied at the input 206-1.

The output 206-3 is connected to an inverting input 211-1 of an operational amplifier 211. A non-inverting input 211-2 is connected to receive a positive potential reference voltage at the junction of a pair of resistors 212 and 213 connected in series between the positive potential system power supply (not shown) and the system ground potential. The positive and negative power supply inputs (not shown) are connected in a manner similar to those of the amplifier 206. A resistor 214 is connected between the positive potential system power supply (not shown) and the output 211-3 to drive a NAND 215 having an input 215-1 connected to the output 211-3. The NAND 215 has an output 215-3 connected to an A signal line 44-1. The positive potential output voltage of the amplifier 206 exceeds the magnitude of the reference voltage at the input 211-2 to generate the system ground potential at the input 215-1. The NAND 215 generates a "1" on the line 44-1 to indicate the absence of a defect.

If one of the signals at the inputs of the NAND 202 goes to "0", the NAND 202 will generate a "1" and the amplifier 206 output signal will drop to the system ground potential with a relatively fast time constant. The amplifier 211 will then generate a positive potential voltage to place a "1" at the input 215-1 to enable the NAND 215. When the defect has passed, the signal at the input 206-1 goes to "0" and the output 206-3 will begin to return to the positive potential voltage as the capacitor 208 charges through the resistor 209 with a relatively slow time constant. If the other signal at the inputs of the NAND 202 does not go to "0" before the amplifiers 206 and 211 change the signal at the input 215-1 back to "0", the NAND 215 will continue to generate a "1". Such a condition is shown in FIG. 8C. If the other signal does go to "0" before the change, the remainder of the circuitry shown in FIG. 7 will change the signal at an input 215-2 from "0" to "1" so that both inputs to the NAND 215 are at "1" and a "0" is generated on the line 44-1 to indicate the presence of a defect. Such conditions are shown in FIGS. 8A and 8B.

The line 41-10 is connected to an input 216-1 of a NAND 216 through an inverter 217 and the line 41-14 is connected to an input 218-2 of a NAND 218 through an inverter 219. The output 211-3 of the amplifier 211 is connected to an input 216-2 of the NAND 216 and to an input 218-1 of the NAND 218 through an inverter 221. An output 216-3 of the NAND 216 and an output 218-3 of the NAND 218 are connected to a pair of inputs 222-1 and 222-2 respectively of a NAND flip flop 222. An output 222-3 and an output 222-4 are connected to an input 223-2 of a NAND 223 and an input 224-1 of a NAND 224 respectively. An input 223-1 of the NAND 223 is connected to the output of the inverter 217 and an input 224-2 of the NAND 224 is connected to the output of the inverter 219. An output 223-3 of the NAND 223 and an output 224-3 of the NAND 224 are connected to a pair of inputs 225-1 and 225-2 respectively of a NAND 225 having an output 225-3 connected to the input 215-2 of the NAND 215. When the ABI— and ATI— signals are both at "1", the inverters 217 and 219 will generate a "0" at the inputs 223-1 and 224-2 to place both inputs of the NAND 225 at "1" and generate a "0" at the input 215-3.

If for example, a defect is detected by the top "1" cell, the ATI— signal will go to "0" and the inverter 217 will place a "1" at the inputs 216-1 and 224-2. The output of the inverter 221 will remain at "1" for a short time before changing to "0" as the amplifier 206 changes its output to the system ground potential with the relatively short time constant. Therefore, both inputs to the NAND 216 will be at "1" for a brief period to generate a "0" at the input 222-1. The ABI— signal is at "1" to generate a "1" at the input 222-2 and the flip flop is set to "1" at the output 222-3 and to "0" at the output 222-4. The NAND 224 receives a "0" at the input 224-1 from the output 222-4 to generate a "1" at the input 225-2. The "1" ABI— signal generates a "0" at the input 223-1 to generate a "1" at the input 225-1. With both inputs at "1", the NAND 225 will continue to generate a "0" at the input 215-2 and maintain the A signal at "1".

If the defect is detected by the bottom "A" cell simultaneously with or within the delay time of the amplifier 206 after the detection by the top "A" cell as shown in FIGS. 8A and 8B, the inverter 219 will generate a "1" at the input 223-1 and the output 222-3 generates a "1" at the input 223-2 to generate a "0" at the output 223-3. The NAND 225 generates a "1" and, with both inputs at "1", the NAND 215 generates a "0" to indicate the detection of a defect by both cells of the "A" pair within a predetermined horizontal distance on the container wall. When the defect has passed, the ABI— signal returns to "1" to place both inputs of the NAND 225 at "1" to generate a "0" at the input 215-2 and change the A signal on the line 44-1 back to "1". If the ABI— signal changes to "0" after the amplifier 206 output has returned to the positive potential voltage as shown in FIG. 8C, the amplifier 211 will have generated a "0" at the input 215-1 to maintain the A signal at "1".

In summary, one portion of the probe logic circuit 44 monitors the ABI— and ATI— signals to generate the A= "0" signal on the line 44-1 when the "A" cells detect a defect or a seam within three-eights of an inch of each other and to generate the (ABI—) + (ATI—) + "0" signal on the line 44-2 when either or both "A" cells detect a defect or a seam. Both "0" signals are only generated during the time the defect or seam is in front of the cell or cells. The other portion of the circuit 44, shown as a block 201, is substantially the same as the circuitry shown. The circuit 201 monitors the BBI— and BTI— signals to generate the B= "0" signal on the line 44-3 when the "B" cells detect a defect or a seam within three-eighths of an inch of each other and to generate the (BBI—) + (BTI—) = "0" signal on the line 44-4 when either or both "B" cells detect a defect or a seam. Both "0" signals are only generated during the time the defect or seam is in front of the cell or cells.

A line 43-2 is connected to an anode of a diode 226 through a capacitor 227 and a resistor 228 connected in series. The diode 226 has its anode connected to the system ground potential through a resistor 229 and has a cathode connected to the input 206-2 of the amplifier 206. The detector channel circuit 43 of FIG. 9 generates a logic signal designated as D on the line 43-2. The D signal is at the "0" logic level when an inspection of a container begins. The anode of the diode 226 is at the system ground potential and the diode is reverse biased by the VD signal to maintain the input 206-2 at the positive potential VD signal level. After the container has been rotated past the cells by a predetermined distance, typically two-tenths of an inch measured horizontally along the outer wall of the container, the D signal will change to "1" to generate a positive going pulse from the capacitor 227 to forward bias the diode 226 through the relatively low value resistor 228. If the amplifier 206 has been integrating in response to a "0" at the output 202-3, the positive going pulse will tend to force the integration to completion in a short time due to the low value of the resistor 228 to ready the circuit for the next detection.

Figure 9:
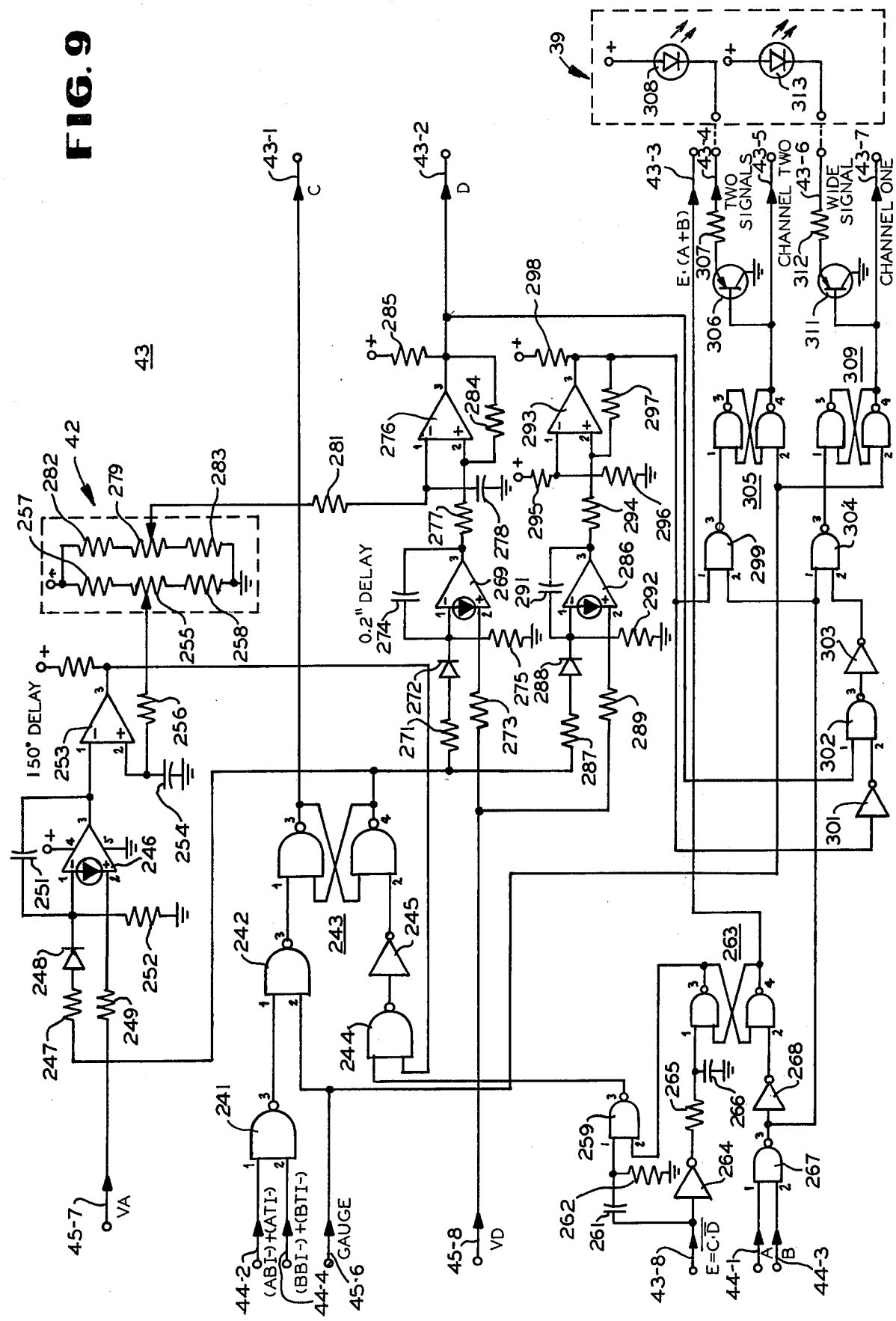
Figure 12:
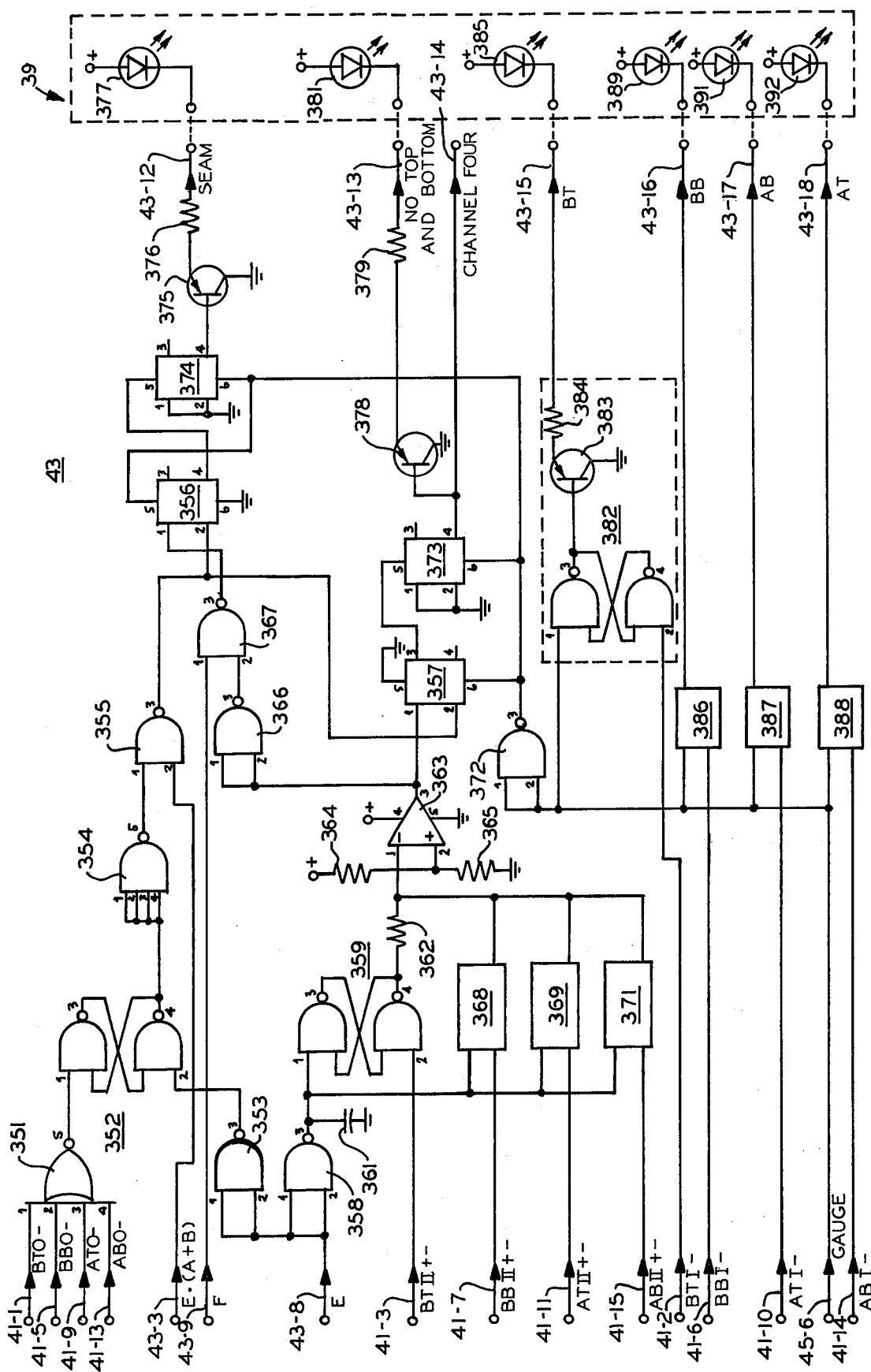

There are shown in FIGS. 9, 11 and 12 the detector channel circuits 43 of FIG. 1. Referring to FIG. 9, there are shown channels one and two wherein the (ABI—) + (ATI—) and (BBI—) + (BTI—) signals from the probe logic circuit 44 of FIG. 7 are monitored. The circuit of FIG. 9 is responsive to a second detection within 150° of a first detection indicating that a defect has been detected since seams are approximately 180° apart and detects the presence of a wide signal within predetermined time limits. FIGS. 10A and 10B are wave form diagrams of the various signals generated in the circuit of FIG. 9 for two sets of input signal conditions.

The (ABI—) + (ATI—) signal on the line 44-2 and the (BBI—) + (BTI—) signal on the line 44-4 are applied to a pair of inputs 241-1 and 241-2 respectively of a NAND 241 having an output 241-3 connected to an input 242-1 of a NAND 242. The GUAGE signal on the line 45-6 is applied to an input 242-2 of the NAND 242 and an output 242-3 is connected to an input 243-1 of a NAND flip-flop 243. When a container is ready for inspection, the GUAGE signal will change from "0" to "1" to enable the NAND 242 to set the NAND flip flop 243 when a defect is detected as one or both of the input signals to the NAND 241 will be at "0" to generate a "1" at the input 242-1 and a "0" at the input 243-1. A reset input 243-2 is connected to an output 244-3 of a NAND 244 through an inverter 245. If we assume that the flip flop was reset by a "0" at either one of a pair of inputs 244-1 and 244-2 of the NAND 244 while the input 243-1 was at "1", the flip flop 243 will generate a "0" on the C signal line 43-1 connected to an output 243-3 and a "1" at an output 243-4.

The output 243-4 is connected to an inverting input 246-1 of a "Norton" operational amplifier 246 through a resistor 247 and a diode 248 having an anode connected to the resistor 247 and a cathode connected to the input 246-1. The amplifier 246 has a non-inverting input 246-2 connected to an input line 45-7 through a resistor 249. The line 45-7 carries the VA signal which is a positive potential voltage having a magnitude proportional to the rotational speed of the container and is generated by the interface circuit 45 of FIG. 14. The amplifier also has an output 246-3 connected to the input 246-1 through a capacitor 251 and the input 246-1 is connected to the system ground potential through a resistor 252. The amplifier 246 has a positive power supply input 246-4 and a negative power supply input 246-5 connected to the positive potential system power supply (not shown) and the system ground potential respectively as do all the other operational amplifiers shown in FIG. 9. The "1" from the output 243-4 exceeds the signal VA in magnitude such that the amplifier 246 generates the system ground potential at the output 246-3 to charge the capacitor 251. The amplifier 246 functions with an operational amplifier 253 to delay a change to "0" in the signal at the input 246-1 by a time period representing 150° of rotation such that a defect, which is always spaced 90° or less from a seam, can be detected.

The output 246-3 is connected to an inverting input 253-1 of the operational amplifier 253. A non-inverting input 253-2 is connected to the system ground potential through a capacitor 254 and to a tap of a potentiometer 255 through a resistor 256 to receive a reference voltage. One end of the potentiometer is connected to the positive potential system power supply (not shown) through a resistor 257 and the other end is connected to the system ground potential through a resistor 258. The potentiometer 255 qnd the resistors 257 and 258 are located in the control circuit 42 of FIG. 1 and generate a channel two time control reference signal corresponding in magnitude to the output signal from the amplifier after a 150° delay. Since the input 253-1 is at the system ground potential, the amplifier 253 will generate the positive potential system power supply voltage at an output 253-3 connected to the input 244-2 to apply a "1".

An input line 43-8 for the E signal generated by the detector channel circuit of FIG. 11 is connected to an input 259-1 for a NAND 259 through a capacitor 261. Under steady state conditions, a "0" is applied to the input 259-1 through a resistor 262 connected to the system ground potential. The NAND 259 has an output connected to the input 244-1 to generate a "1". With both inputs at "1", the NAND 244 generates a "0" which is changed to a "1" at the input 243-2. Thus, the flip flop 243 maintains the assumed output signals.

The line 43-8 is also connected to an input 263-1 of a NAND flip flop 263 through an inverter 264 and a resistor 265. A capacitor 266 is connected between the input 263-1 and the system ground potential. As will be shown later, the E signal is at "1" before a defect is detected to apply a "0" at the input 263-1 and set an output 263-4 at "0". The output 243-4 is connected to a line 43-3 to output a signal designated E · (A+B), the A and B being generated by the probe logic circuit 44 of FIG. 7. The A line 44-1 is connected to an input 267-1 and the B line 44-3 is connected to an input 267-2 of a NAND 267 having an output 267-3 connected to an input 263-2 of the flip flop 263 through an inverter 268. Before a defect is detected both A and B are at "1" to generate a "1" at the input 263-2 and a "1" at an output 263-3 connected to an input 259-2 of the NAND 259.

The output 243-4 of the flip flop 243 is also connected to an inverting input 269-1 of a "Norton" operational amplifier 269 through a resistor 271 and a diode 272 having an anode connected to the resistor 271 and a cathode connected to the input 269-1. The amplifier 269 has a non-inverting input 269-2 connected to the input line 45-8 through a resistor 273 to receive the VD signal generated by the interface circuit 45 of FIG. 14. The amplifier also has an output 269-3 connected to the input 269-1 through a capacitor 274 and the input 269-1 is connected to the system ground potential through a resistor 275. The "1" from the output 243-4 exceeds the signal VD in magnitude such that the amplifier 269 generates the system ground potential at the output 269-3 to charge the capacitor 274. The amplifier 269 functions with an operational amplifier 276 to delay a change to "0" in the signal at the input 269-1 by a time period representing two tenths of an inch of rotation such that, if at least one of the pairs of cells detects a defect or seam in that time period, the flip flop 243 can only be reset by the 150° delay signal and a second detection before the reset will light a TWO SIGNALS indicator light.

The output 269-3 is connected to a non-inverting input 276-2 of an operational amplifier 276 through a resistor 277. An inverting input 276-1 is connected to the system ground potential through a capacitor 278 and to a tap of a potentiometer 279 through a resistor 281 to receive a reference voltage. One end of the potentiometer is connected to the positive potential system power supply (not shown) through a resistor 282 and the other end is connected to the system ground potential through a resistor 283. The potentiometer 279 and the resistors 282 and 283 are located in the control circuit 42 of FIG. 1 and generate a channel one time control reference signal corresponding in magnitude to the output signal from the amplifier after a two tenths of an inch of rotation delay. The input 276-2 is connected to an output 276-3 through a resistor 284 for positive feedback to operate in saturation. The output 276-3 is connected to the positive potential system power supply (not shown) through a resistor 285 to drive the following circuits and to an output line 43-2 to generate the D output signal. Since the input 276-2 is at the system ground potential, the amplifier 276 will generate the system ground potential at the output 276-3 to supply a "0".

Referring to FIGS. 9 and 10A, when at least one of the cells detects a defect or a seam, one of the inputs to the NAND 241 will be at "0" to generate a "1" at the input 242-1. With both inputs at "1", the NAND 242 will generate a "0" at the input 243-1 to set the flip flop 243 and change the output signals. The output 243-3 will go to "1" to change the C signal on the line 43-1 and the output 243-4 will go to "0" to reverse bias the diode 248. The capacitor 251 will begin to discharge and charge in the opposite direction through the resistor 249 as the output voltage increases. The "0" at the output 243-4 will also reverse bias the diode 272 and the capacitor 274 will begin to discharge and charge in the opposite direction through the resistor 273 as the output voltage increases.

The C and D signals are the inputs to the circuit of FIG. 11 which responds to generate the E signal as the NAND of the C and the D signals. When the C signal changes to "1", the E signal changes to "0". The "0" is changed to a "1" by the inverter 264 and delayed by the capacitor 266. If one or both of the pairs of cells has detected a defect, the NAND 267 will generate a "0" at the input 263-2 to set the flip flop 263 to generate a "0" at the output 263-3 to the input 259-2 of the NAND 259. Thus, the NAND 259 is disabled from resetting the flip flop 243 upon a subsequent change to "1" by the D signal after the delay of two tenths of an inch.

When the signal at the output 269-3 exceeds the channel one reference voltage, the amplifier 276 will generate a "1" which changes the E signal back to "1". The capacitor 261 responds to the change in the E signal to generate a positive going pulse at the input 269-1. However, since the output 263-3 is at "0", the NAND 269 will continue to generate a "1". After a short time delay, the signal at the input 263-1 will change to "0" and the flip flop will invert its output signals to apply a "1" at the input 259-2 and a "0" on the line 43-3. However, since the positive going pulse at the input 259-1 has decayed to "0", the NAND 259 will continue to generate a "1".

The flip flop 243 will only be reset when the 150° delay time is completed. When the voltage across the capacitor 251 and at the output 246-3 reaches the magnitude of the channel two reference voltage at the input 253-2, the amplifier 253 will change its output signal to the system ground potential to apply a "0" at the input 244-2 and the input 243-2 to reset the flip flop. The output 243-3 will change to "0" on the C line 43-1 and the output 243-4 will change to "1" thereby switching the outputs of the amplifiers 269 and 276 and changing the D signal on the line 43-2 to "0". The "1" at the output 243-4 also switches the amplifiers 246 and 253 to return the inputs 244-2 and 243-2 to "1". Thus, the circuit is ready to detect a subsequent defect or seam and the assumed initial conditions have been proved as shown in FIG. 10A.

If only one of the cells of a pair or both pairs detect a defect such as a bubble in the wall or detect a portion of a light seam, the A and B signals will not be generated and the outputs 263-3 and 263-4 will remain at "1" and "0" respectively. When the D signal switches to "1" at the end of the two tenths of an inch delay, the E signal will switch to "0" as before to generate a positive going pulse at the input 259-1. Since the input 259-2 is also at "1", a "0" will be generated at the inputs 244-1 and 243-2 to reset the flip flop 243 in the same manner as did the 150° delay. Thus, the circuit of FIG. 9 will not recognize a bubble or a light seam as a ribbon tear defect. Such operation is shown in FIG. 10B.

The A, B and D signals and the signal at the flip flop output 243-4 are utilized to indicate the detection of a defect or seam before the 150° delay has ended and the detection of a defect having a width of between two tenths of an inch and seven tenths of an inch. The output 243-4 is connected to an inverting input 286-1 of a "Norton" operational amplifier 286 through a resistor 287 and a diode 288 having an anode connected to the resistor 276 and a cathode connected to the input 286-1.

The amplifier 286 has a non-inverting input 286-2 connected to the VD input line 45-8 through a resistor 289 and an output 286-3 connected to the input 286-1 through a capacitor 291. The input 286-1 is also connected to the system ground potential through a resistor 292. The "1" from the output 243-4 exceeds the signal VD in magnitude such that the amplifier 286 generates the system ground potential at the output 286-3 to charge the capacitor 291. The amplifier 286 functions with an operational amplifier 293 to delay a change to "0" in the signal at the input 286-1 by a time period representing seven tenths of an inch of rotation such that, if at least one of the pairs of cells detects a defect or a seam between two tenths and seven tenths of an inch of rotation, a WIDE SIGNAL is indicated and a detection between seven tenths and 150° will indicate TWO SIGNALS.

The output 286-3 is connected to a non-inverting input 293-2 of the operational amplifier 293 through a resistor 294. An inverting input 293-1 is connected to the positive potential system power supply (not shown) through a resistor 295 and to the system ground potential through a resistor 296 to receive a reference voltage representing seven tenths of an inch of rotation. The input 293-2 is connected to an output 293-3 through a resistor 297 for positive feedback to operate in saturation. The output 293-3 is connected to the positive potential system power supply (not shown) through a resistor 298 to drive the following circuits, to an input 299-1 of a NAND 299 and through an inverter 301 to an input 302-1 of a NAND 302.

The NAND 302 has an input 302-1 connected to the output 276-3 to receive the D signal and an output 302-3 connected through an inverter 303 to an input 304-2 of a NAND 304. The output 267-3 of the NAND 267, which receives the A and B signals, is connected to an input 299-2 of the NAND 299 and an input 304-1 of the NAND 304. A NAND flip flop 305 has an input 305-1 connected to the output 299-3, an input 305-2 connected to the GUAGE line 45-6 and an output 305-4 connected to a line 43-5 for generating the CHANNEL TWO signal indicating two signals have been received. The output 305-4 is also connected to a base of a PNP transistor 306 having an emitter connected to the system ground potential and a collector connected to a line 43-4 through a current limiting resistor 307. The line 43-4 is connected to a cathode of an external photoemissive or light emitting diode 308 included in the indicators and counters 39 of FIG. 1 and having an anode connected to a positive potential external power supply. A NAND flip flop 309 has an input 309-1 connected to the output 304-3 of the NAND 304, an input 309-2 connected to the GUAGE line 43-5 and an output 309-4 connected to a line 43-7 for generating the CHANNEL ONE signal indicating a wide signal has been received. The output 309-4 is also connected to a base of a PNP transistor 311 having an emitter connected to the system ground potential and a collector connected to a line 43-6 through a current limiting resistor 312. The line 43-6 is connected to a cathode of an external photoemissive or light emitting diode 313 included in the indicators and counters 39 of FIG. 1 and having an anode connected to a positive potential external power supply.

Before an inspection begins, the GUAGE signal will be at "0" which signal is applied to the inputs 305-2 and 309-2. The A and B signals will be at "1" to generate a "0" at the inputs 299-2 and 304-1 and a "1" at the inputs 305-1 and 309-1. Therefore, the NAND flip flops 305 and 309 will generate a "1" on the lines 43-5 and 43-7 to indicate the absence of a signal detection. The "1" signal will also turn off the transistors 306 and 311 so that no current flows through the diodes 308 and 313. When an inspection begins, the GUAGE signal will change to "1" but the other signals will remain the same.

When a defect or seam is detected, at least one of the A and B signals goes to "0" to generate a "1" at the inputs 299-2 and 304-1 to enable the NAND's 299 and 304. For the first two tenths of an inch after the detection, the amplifier 276 will continue to generate a "0" to apply a "0" to the input 302-1 to generate the "0" at the input 304-2. When the D signal changes to "1", both inputs to the NAND 302 will be at "1" and "1" will be generated at the input 304-2. After seven tenths of an inch of rotation, the amplifier 293 will change to "1" and the input 304-2 will return to "0". Therefore, there is a "window" between two tenths and seven tenths of an inch of rotation during which the NAND 304 is enabled by a "1" at the input 304-2.

If either or both of the A and B signals are at "0" during the "window", the NAND 304 will generate a "0" to set the flip flop 309 to "0" at the output 309-4. The signal on the CHANNEL ONE line 43-7 goes to "0" and the transistor 311 is turned on to ground the cathode of the diode 313 permitting current flow for a visual indication that a WIDE SIGNAL was received. Such operation will occur if a ribbon tear defect is detected which extends at least partially beyond the two tenths of an inch of rotation from the initial detection or if a seam and a ribbon tear are in the range of two tenths to seven tenths of an inch apart. Since seams are always relatively narrow, a single seam will not generate the first type of WIDE SIGNAL detection.

After the "window" passes, the amplifier 293 will generate a "1" at the input 299-1 to enable the NAND 299 until the 150° delay resets the flip flop 243. If either or both of the A and B signals are "0" during this time period, the NAND 299 will generate a "0" to set the flip flop 305 to "0" at the output 305-4. The signal on the CHANNEL TWO line 43-4 goes to "0" and the transistor 306 is turned on to ground the cathode of the diode 308 permitting current flow for a visual indication that two signals were received within 150° of each other. Since the seams are approximately 180° apart, one of the signals is a ribbon tear defect. The flip flops 305 and 309 are reset when the GUAGE signal goes to "0" between inspections.

In summary, the circuit of FIG. 9 shows channels one and two of the detector channel circuits 43 of FIG. 1. The (ABI−) + (ATI−), (BBI−) + (BTI−), A and B signals from the probe logic circuit 44 of FIG. 7 are monitored for detections by one or more of the cells at the normal signal level. A detection by at least one cell enables three timing circuits. If there is no detection by at least one of the two pairs of cells prior to the rotation of the container through two tenths of an inch after an initial detection, a first timing circuit will reset all the circuitry ignoring the initial detection. If there is detection by at least one of the pairs of cells, the first timing circuit and another timing circuit form a "window" between two tenths and seven tenths of an inch of rotation to detect a wide single defect or a defect relatively closely spaced to a seam. The second and third timing circuits cooperate to enable the circuitry to respond to a second detection between seven tenths of an inch and 150° of rotation to detect a defect spaced from a seam. The WIDE SIGNAL and TWO SIGNALS detections light indicators and generate output signals to the interface circuit 45 of FIG. 14.

Referring to FIG. 11, there is shown another portion of the detector channel circuits 43 of FIG. 1, the channel three detector circuit. The ABII−, ATII−, BBII− and BTII− signals are monitored to detect a defect within two tenths of an inch of a seam which otherwise would not be detected by channel one as a wide signal. The signal from each cell is grouped with the signal from the two cells of the other pair to detect a difference between the width of the top and bottom of the defect or seam. If the widths are substantially the same, it is determined that a seam has been detected. If the widths differ by more than a predetermined amount, a TOP AND BOTTOM indicator is lighted and a CHANNEL THREE signal is generated since a defect is seldom substantially the same width at the top and bottom as is a seam.

The ABII−, ATII−, BBII− and BTII− signals are received on the lines 41-16, 41-12, 41-8 and 41-4 respectively from the comparators 41 of FIG. 5. Each signal is grouped with the two signals from the other pair of cells as inputs to one of four detection circuits with their outputs connected together. Only one of the circuits will be discussed in detail as the other three function in a similar manner. The BTII− line 41-4 is connected to an input 321-1 of a triple input NAND 321 and an input 322-1 of a triple input NOR 322. The BBII− line 41-8 is connected to an input 321-2 and an input 322-2 and the ATII− line 41-12 is connected to an input 321-3 and an input 322-3. Thus, the "B" pair of cells is grouped with the "AT" cell. The NAND 321 will generate a "0" at an output 321-4 when all the inputs are at "1" representing no detection by any of the three cells and will generate a "1" if one or more inputs are at "0" representing a detection by one or more of the three cells. The NOR 322 will generate a "1" at an output 322-4 when all the inputs are at "0" representing a detection by all three cells and will generate a "0" if one or more of the inputs are at "1" representing no detection by one or more of the three cells.

The output 321-4 is connected to an input 323-1 of an exclusive-OR 323 and the output 322-4 is connected to an input 323-2. If both input signals are the same, the exclusive-OR will generate a "0" at an output 323-3 and will generate a "1" if the input signals are different. Thus, the output 323-3 will be at "0" if the three grouped signals are the same and will be at "1" if one of the three is different. The output 323-3 is connected to a gate of a P-channel field effect transistor (FET) 324 having a source connected to the system ground potential and a drain connected to the VD line 45-8 through a resistor 325. A "0" at the gate will turn on the FET 325 and a "1" will turn it off. The drain is also connected to the positive potential system power supply (not shown) through a resistor 326 and to a non-inverting input 327-2 of a "Norton" operational amplifier 327. The amplifier 327 has an inverting input 327-1 connected to an output 327-3 through a capacitor 328 and a positive power supply input 327-4 and a negative power supply input 327-5 connected to the positive potential system power supply (not shown) and the system ground potential respectively.

The C signal line 43-1 from the detector channel circuits of FIG. 9 is connected to an input 329-1 of a NAND 329 and the D signal line 43-2 is connected to an input 329-2 through an inverter 331. The NAND 329 has an output 329-3 which is connected to the line 43-8 to generate the E signal as was previously discussed in connection with FIGS. 9, 10A and 10B. The output 329-3 is also connected to a base of a NPN transistor 332 having a collector connected to the positive potential system power supply (not shown) and an emitter connected to the amplifier input 327-1 through a resistor 333 connected to an anode of a diode 324 having a cathode connected to the input 327-1.

Before a seam or a defect is detected, the C and D signals are at "0" to generate a "1" at the output 339-3 and turn on the transistor 332 to apply the positive potential system power supply voltage to the amplifier input 327-1. The three cell signals will be at "1" to generate a "0" at the output 323-3 to turn on the FET 324 and apply the system ground potential to the input 327-2. The amplifier 327 will generate the system ground potential at the output 327-3 which is connected to a non-inverting input 335-2 of an operational amplifier 335. An inverting input 335-1 is connected to a tap of a potentiometer 336 in the control circuit 42 of FIG. 1. The potentiometer has one end connected to the positive potential system power supply (not shown) and the other end connected to the system ground potential to provide a reference voltage equal in magnitude to the output voltage from the amplifier 327 reached after an integration time representing a predetermined distance rotated wherein one cell signal is different from the other two. A capacitor 338 is connected between the input 335-1 and the system ground potential with the resistor 337 and the capacitor 338 functioning as a low pass filter.

An output 335-3 of the amplifier 335 is connected to the positive potential system power supply (not shown) through a resistor 339 to drive the following circuits. The output 335-3 is connected to an input 341-1 of a NAND 341 having an input 341-2 connected to the line 43-3 to receive the E·(A+B) signal and an output connected to an input 342-1 of a NAND flip flop 342 and an output line 43-9 to generate an F signal to the circuit of FIG. 12. The amplifier 335 also has positive and negative power supply inputs (not shown) connected in a manner similar to those of the amplifier 327. The amplifier 335 will generate the system ground potential at the output 335-3 to generate a "1" at the input 342-1. An input 343-2 is connected to the GUAGE line 45-6. Before an inspection cycle begins, the line 45-6 will be at "0" such that a "1" is generated at an output 342-4. When the GUAGE signal goes to "1", the flip flop 342 will continue to generate "1" at the output 342-4 which is connected to a CHANNEL THREE signal line 43-10 and a base of a PNP transistor 343. A collector of the transistor 343 is connected to the system ground potential and an emitter is connected to a TOP AND BOTTOM line 43-11 through a resistor 344. The line 43-11 is connected to a cathode of a LED 345 having an anode connected to an external positive potential power supply (not shown), the LED and power supply being located in the indicator and counters circuit 39. The transistor 343 is turned off to prevent current flow through the LED 345.

When a defect or a seam is detected, the C signal will change to "1" to generate a "0" from the NAND 329 to turn off the transistor 332 and remove the positive potential voltage from the input 327-1 of the amplifier 327. The amplifier 327 will generate a sawtooth wave form limited by the positive potential system power supply voltage and terminated when the D signal changes to "1" after two tenths of an inch of rotation. However, during the two tenths of an inch of rotation, the integration or ramping generating the sawtooth will be stopped if all three II-signals are the same since the associated FET will be turned on. Therefore, the amplifier 327 output reaches a voltage representing the time the signals were different. For example, if a seam is detected by all four of the cells wherein the cell signals change to "0", the amplifiers 326 and 335 will continue to generate the system ground potential. If a defect is adjacent the seam or a defect was detected instead of the seam, one or more of the cell signals in any one of the four groups of three may go to "1" before the D signal goes to "1". If for example, the top of the defect terminates before the bottom or the defect is short without a top portion, the ATII-signal will return to "1" turning off the FET 324 and the two other FET's indirectly connected to the ATII-signal. The amplifier 327 will now begin to generate the sawtooth wave form and, when its magnitude exceeds the reference voltage at the input 335-1, the amplifier 335 will switch to the positive potential system power supply voltage. However, since one of the four circuits is not connected to the ATII− line 43-12, its associated amplifier will continue to generate a "0" at the input 341-1 to disable the NAND 341. The circuits will function in a similar manner if three of the cell signals go to "1" before the D signal goes to "1".

If two of the cell signals go to "1", all of the amplifiers connected to the input 341-1 will switch to the positive potential system power supply voltage to apply a "1" to the input 341-1 of the NAND 341. Since the input 341-2 receives the E·(A+B) signal which is at "1" between the time of detection when the C signal goes to "1" and the end of the two tenths of an inch delay when the D signal goes to "1" if the two cell signals which went to "1" are in the same pair, the NAND 341 will generate a "0" on the line 43-9 as the F signal and at the input 342-1 to set the flip flop 342 to generate a "0" at the output 342-4. Thus, the CHANNEL THREE signal goes to "0" and the transistor 343 is turned on to light the LED 345 to indicate a short defect or a difference in width between the top and bottom of the detected defect. The amplifiers 327 and 335 are reset when the D signal goes to "1" since more than one seam and/or defect may be detected during an inspection cycle. The flip flop 342 is reset when the GUAGE signal goes to "0" between inspections.

In summary, the channel three detector circuit 43 of FIG. 11 monitors the ABII−, ATII−, BBII− and BTII− signals to detect ribbon tear defects which have variations in width between the top and the bottom occurring within two tenths of an inch of the initial detection of a seam or a defect. Such a defect will generate a CHANNEL THREE output signal on the line 43-10 and light a TOP AND BOTTOM indicator LED.

Referring to FIG. 12, there is shown a schematic diagram of the channel four portion of the channel detector circuits 43 of FIG. 1. This circuit monitors the signals representing the O−, I− and II+ − comparisons with each cell output signal to distinguish between a seam and a skewed ribbon tear or a short tear during the first two tenths of an inch of rotation. Upon the detection of a scan, a SEAM indicator is lighted and upon the detection of a short or a skewed ribbon tear, a NO TOP AND BOTTOM indicator is lighted and a CHANNEL FOUR signal is generated. Indicators are also provided for the normal level detections by each of the four cells.

The BTO− signal line 41-1, the BBO− signal line 41-5, the ATO− signal line 41-9 and the ABO− signal line 41-13 from the comparators 41 of FIG. 5 are connected to inputs 351-1, 351-2, 351-3 and 351-4 respectively of a quad input NOR 351 having an output 351-5 connected to an input 352-1 of a NAND flip flop 352. The E signal line 43-8 from the channel three circuit of FIG. 11 is connected to a pair of inputs 353-1 and 353-2 of a NAND 353 which functions as an inverter and has an output 353-3 connected to an input 352-2 of the flip flop 352. The flip flop 352 has an output 352-4 connected to all four inputs of a quad input NOR 354 which also functions as an inverter and has an output 354-5 connected to an input 355-1 of a NAND 355. The NAND 355 has an input 355-2 connected to the E·(A+B) signal line 43-3 from the channels one and two circuit of FIG. 9 and an output 355-3 is connected to a pair of clock inputs 356-2 and 357-2 of a pair of D-type flip flops 356 and 357 respectively.

The flip flop 356 has a data input 356-1 wherein the input signal is transferred to a non-inverting output 356-3 and is inverted at an inverting output 356-4 when the signal at the clock input 356-2 switches from "0" to "1". A "1" at a set input 356-5 will generate a "1" at the output 356-3 and a "0" at the output 356-4, a "1" at a reset input 356-6 will generate a "0" at the output 356-3 and a "1" at the output 356-4 and a "1" at both the set and reset inputs will generate a "1" at both of the outputs.

The E signal line 43-8 from the circuit of FIG. 11 is connected to a pair of inputs of a NAND 358 which functions as an inverter and has an output 358-3 connected to an input 359-1 of a NAND flip flop 359. A capacitor 361 is connected between the input 359-1 and the system ground potential to delay a signal change between the output 358-3 and the input 359-1. The BTII+ − line 43-3 is connected to an input 359-2 of the flip flop 359 which has an output 359-4 connected through a resistor 362 to an inverting input 363-1 of an operational amplifier 363. The amplifier 363 has a non-inverting input 363-2 connected to the positive potential system power supply (not shown) through a resistor 364 and to the system ground potential through a resistor 365 to provide a reference signal having a magnitude of approximately three-fourths the positive potential system power supply voltage. The amplifier has an output 363-3 connected to a data input 357-1 of the flip flop 357 and to a pair of inputs of an NAND 366 which functions as an inverter. The NAND 366 has an output 366-3 connected to an input 367-2 of a NAND 367 having an input 367-1 connected to the F line 43-9 and an output 367-3 connected to the data input 356-1 of the flip flop 356.

The output 358-3 is also connected to an input of each of three blocks 368, 369 and 371, each block representing a NAND flip flop and output resistor similar to the flip flop 359 and the resistor 362. A second input of each of the blocks is connected to one of the II+ − signal lines, the BBII+ − lines 41-3 being connected to the block 368, the ATII+ − line 41-11 being connected to the block 369 and the ABII+ − line 41-15 being connected to the block 371 and each block has an output connected to the input 363-1 of the amplifier 363. The above-described circuits monitor the O− and II+ − signals to distinguish between a seam and ribbon tear defect.

Before a detection is made, all of the inputs to the NOR 351 are at "0" to generate a "1" at the input 352-1.

The E signal is at "1" to generate a "0" at the input 352-2 and a "1" at the output 352-4. The NOR 354 will generate a "0" to disable the NAND 355 and generate a "1" at the clock inputs 346-2 and 357-2. The E signal will also generate a "0" at the −1 inputs of each of the four NAND flip flops for the II+ − signals to generate a "0" at the data input 357-1 and enable the NAND 367 with a "1" at the input 367-2. The E·(A+B) signal is at "0" to generate a "1" at the data input 356-1. The GUAGE line 45-6 is connected to a pair of inputs of a NAND 372 which functions as an inverter and has an output 372-3 connected to a reset input 357-6 of the flip flop 357 and to the set input 356-5 of the flip flop 356. Since the reset input 356-6 and a set input 357-5 are connected to the system ground potential, the flip flop 356 will generate a "0" at the output 356-4 and the flip flop 357 will generate a "0" at a non-inverting output 357-3.

The flip flop output 357-3 is connected to a set input 373-5 of a D-type flip flop 373 having a data input 373-1 and a clock input 373-2 connected to the system ground potential. A reset input 373-6 is connected to the output 372-3 to receive a "1" and generate a "1" at an inverting output 373-4. The output 356-4 is connected to a set input 374-5 of a D-type flip flop 374 having a data input 374-1 and a clock input 374-2 connected to the system ground potential. A reset input 374-6 is connected to the output 372-3 to receive a "1" and generate a "1" at an inverting output 374-4. The output 374-4 is connected to a base of a PNP transistor 375 having a collector connected to a SEAM signal output line 43-12 through a resistor 376 and an emitter connected to the system ground potential. The line 43-12 is connected to a cathode of a LED 377 having an anode connected to an external positive potential power supply, the LED and power supply being located in the indicators and counters circuit 39 of FIG. 1. The "1" at the output 374-4 turns off the transistor 375 to prevent current flow through the LED 377. The output 373-4 is connected to a CHANNEL FOUR output signal line 43-14 and to a base of a PNP transistor 378. The transistor 378 has a collector connected to a NO TOP AND BOTTOM signal line 43-13 through a resistor 379 and an emitter connected to the system ground potential. The line 43-13 is connected to a cathode of a LED 381 having an anode connected to an external positive potential power supply, the LED and power supply being located in the circuit 39 of FIG. 1. The "1" at the output 373-4 turns off the transistor 378 to prevent current flow through the LED 377.

When the inspection cycle begins, the GUAGE signal will change to "1" and a "0" will be applied at the set input 356-5 and the reset inputs 357-6, 373-6 and 374-6 to enable the D-type flip flops to respond to a clock signal. If at least two I− signals are generated when a detection is made, the E signal will go to "0" to apply "1" at the input 352-2 and, after a delay caused by the capacitor 362, at the −1 inputs of each of the four flip flops. If only two of the II+ − signals are at "0" indicating a ribbon tear defect, the associated flip flops will generate a "1" at their outputs but the magnitude of the voltage at the input 363-1 will continue to be less than the reference voltage to generate a "1" at the output 363-3. If three or more of the II+ − signals are at "0" indicating a seam, the associated flip flops will generate a "1" at their outputs to apply a voltage at the input 363-1 which will exceed the magnitude of the reference voltage to generate a "0" at the output 363-3.

Thus, the E signal provides a "1" to enable the flip flop 352 at the input 352-2 and the E·(A+B) signal provides a "1" to enable the NAND 367. Since the NAND 355 will generate a "1" when the E signal returns to "1" after two tenths of an inch of rotation and the D-type flip flops transfer data during the "0" to "1" transition at their clock inputs, a change from "1" to "0" at the output 351-5 before the E signal returns to "1" will set the output 355-3 to "0" to enable the "0" to "1" clock signal transition.

If at least one of the O− signals changes to "1", the signal at the output 351-5 will change to "0" to place a "0" at the clock inputs 356-2 and 357-2. If the output 363-3 is at "0" as shown in FIG. 13A, a "0" will be generated at the data input 356-1 when the F signal on the line 43-9 is at "1" and a "0" will be generated at the data input 357-1. As was discussed in connection with the circuit of FIG. 11, the F signal will be at "1" if either three or four of the II− signals are the same and will be at "0" if the two signals from one pair of the cells are different from the two signals of the other pair of cells. Since the output 363-3 is at "0", the F signal will be at "1" to enable the NAND 367. When the E signal returns to "1", the signal at the clock inputs will return to "1" to switch the output 356-4 to "1" and maintain the output 357-3 at "0". The flip flop 374 will be set by the "1" at the set input 374-5 to generate a "0" at the output 374-4. The transistor 375 will be turned on to permit current flow in the LED 377 to provide a visual indication that a seam was detected.

If the output 363-3 is at "1" as shown in FIG. 13B, a "1" will be generated at the data input 357-1 and at the data input 356-1. When the E signal returns to "1", the signal at the clock inputs will return to "1" to switch the output 357-3 to "1" and maintain the output 356-4 at "0". The flip flop 373 will be set by the "1" at the set input 373-5 to generate a "0" at the output 373-4. The transistor 378 will be turned on to permit current flow in the LED 381 to provide a NO TOP AND BOTTOM visual indication that a defect having a difference in width between its top and bottom was detected. The change from "1" to "0" at the output 373-4 also generates a CHANNEL FOUR signal on the line 43-14.

The BTI− signal line 41-2, the BBI− signal line 41-6, the ATI− signal line 41-10 and the ABI− signal line 41-14 are each connected to an input of an associated NAND flip flop to generate visual indications of detections by each of the cells. For example, the line 41-2 is connected to an input 382-2 of a NAND flip flop 382 having an input 382-1 connected to the GUAGE line 45-6. The flip flop 382 also has an output 382-3 connected to a base of a PNP transistor 383 having a collector connected to BT output line 43-15 through a resistor 384 and an emitter connected to the system ground potential. The line 43-15 is connected to a LED and external power source located in the indicators and counters circuit 39 for FIG. 1 such as a LED 385 having an anode connected to an external positive potential power supply (not shown) and a cathode connected to the line 43-15.

Before the inspection cycle begins, the GUAGE signal is at "0" and each of the I− signals is at "1" to generate a "1" at the output 382-3 to turn off the transistor 383 to prevent current flow in the LED 385. During the inspection cycle, the GUAGE signal is at "1" such that, if the BTI− signal goes to "0", the flip flop 382 will generate a "0" to turn on the transistor 383 to permit current flow through the LED 385 and provide a visual indication of the detection by the BT cell. The BBI— line 41-6, the ATI— line 41-10 and the ABI— line 41-14 are connected to an input of a circuit 386, an input of a circuit 387 and an input of a circuit 388 respectively, the circuits 386, 387 and 388 each representing a NAND flip flop, PNP transistor and current limiting output resistor such as those associated with the BT circuit. The circuit 386 has an output connected to a BB output line 43-16 which in turn is connected to a LED 389 to provide a visual indication of a detection by the BB cell. The circuit 387 has an output connected to an AT line 43-17 which in turn is connected to a LED 391 and the circuit 388 has an output connected to an AB line 43-18 which in turn is connected to a LED 392 to generate visual indications of the detections by the AT and AB cells respectively.

In summary, the channel four circuit of the detector channel circuits 43 of FIG. 1 monitors the output signals from the comparators 41 of FIG. 5. When at least one 0— signal and two I— signals are generated, the circuit of FIG. 12 will function to distinguish between a seam and a ribbon tear within the first two tenths of an inch of rotation after the beginning of the detection. If at least three of the four II+ — signals are the same, the circuit will light a LED indicating that a seam has been detected. If two of the II+ — signals are different from the other two II+ — signals, the circuit will light a NO TOP AND BOTTOM LED indicating that a ribbon tear has been detected. The circuit also monitors the I— signals to provide indications of a detection by each of the cells.

Figure 14:
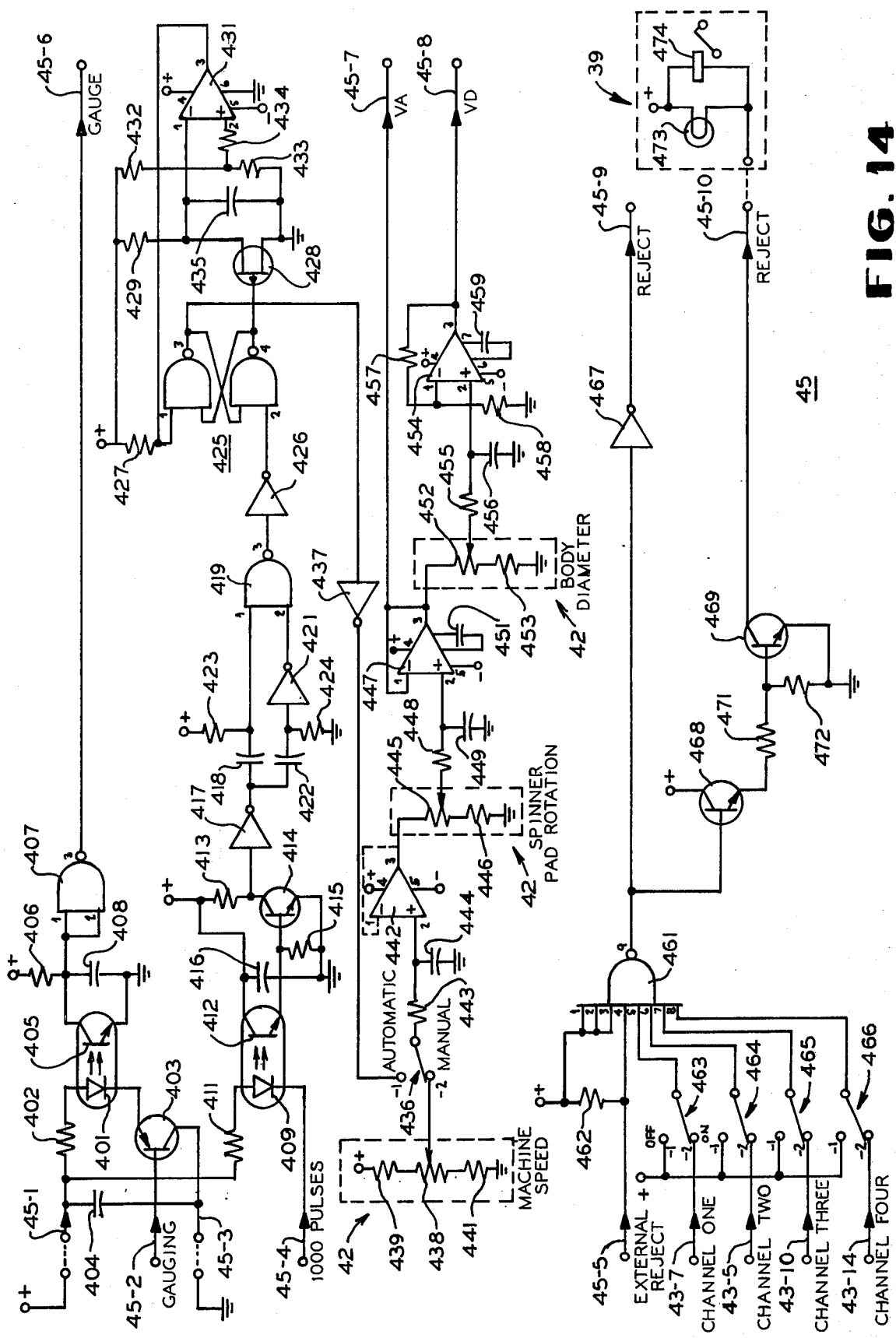
FIG. 14 is a schematic diagram of the interface circuit of FIG. 1.

There is shown in FIG. 14 the interface circuit 45 of FIG. 1 which generates the GUAGE, VA and VD signals. A pair of inputs 45-1 and 45-3 are connected to an external positive potential power supply and ground potential respectively and an input 45-2 is connected to an external source of a GUAGING signal to generate the GUAGE signal on the line 45-6. The line 45-1 is connected to an anode of a photoemissive diode 401 through a current limiting resistor 402. The diode 401 has a cathode connected to an emitter of a PNP transistor 403 having a base connected to the line 45-2 and a collector connected to the line 45-3. A capacitor 404 is connected between the lines 45-1 and 45-3 wherein the resistor 402 and the capacitor 404 function as a low pass filter for the external power supply.

A phototransistor 405 has a collector connected to the positive potential system power supply (not shown) through a resistor 406 and to a pair of inputs 407-1 and 407-2 of a NAND 407 which functions as an inverter. A collector of the transistor 405 is connected to the system ground potential and a capacitor 408 is connected between the collector and the emitter of the transistor. The NAND 407 has an output 407-3 connected to the GUAGE signal line 45-6. Before an inspection cycle begins, the inspection machine applies the external positive potential power supply voltage to the line 45-2 to turn off the transistor 403. No current will flow through the diode 401 and the phototransistor 405 will be turned off to charge the capacitor 408 to the positive potential system power supply. The NAND 407 will generate a "0" on the line 45-6 to indicate the absence of the GUAGING signal. During the inspection cycle, the line 45-2 will be at "0" to turn on the transistor 403 and permit current flow through the diode 401. The light from the diode will turn on the phototransistor 405 to apply the system ground potential to the inputs of the NAND 407 which generates the "1" GUAGE signal on the line 45-6.

The line 45-1 is also connected to an anode of a photoemissive diode 409 through a current limiting resistor 411. The diode has a cathode connected to a line 45-4 which receives a train of clock pulses of constant frequency, typically one thousand pulses per machine cycle, thus the designation 1000 PULSES. The pulse train alternates between the external ground and positive potentials to pulse the diode 409. The phototransistor 412 responds to the alternate dark and pulses of light from the diode to turn off and on respectively. The phototransistor 412 has a collector connected to the positive potential system power supply (not shown) and to a collector of a NPN transistor 414 through a resistor 413. An emitter of the phototransistor 412 is connected to a base of the transistor and to the system ground potential. An emitter of the transistor 414 is connected to the system ground potential and to the base through a resistor 415. A capacitor 416 is connected between the collector of the phototransistor 412 and the emitter of the transistor 414. When the line 45-4 is at the external ground potential, the phototransistor 412 will be turned off and the base of the transistor 414 will be at the system ground potential to turn off the transistor 414. When the line 45-4 is at the external positive potential power supply voltage, the phototransistor 412 will be turned on and the base of the transistor 414 will be biased by the positive potential system power supply voltage to turn on the transistor 414. As the transistor 414 is alternately turned on and off, its collector will alternately be at the system ground potential and the positive potential system power supply voltage.

The collector of the transistor 414 is connected to an input of an inverter 417 having an output connected to an input 418-1 of a NAND 419 through a capacitor 418 and to an input of an inverter 421 through a capacitor 422. The input 419-1 is also connected to the positive potential system power supply through a resistor 423 to apply a "1" at the input 419-1. The input of the inverter 421 is connected to the system ground potential through a resistor 424 and the inverter 421 has an output connected to an input 419-2 to supply a "1". The NAND 419 has an output 419-3 connected to an input 425-2 of a NAND flip flop 425 through an inverter 426. The flip flop has an input 425-1 connected to the positive potential system power supply (not shown) through a resistor 427 and an output 425-4 connected to a gate of a P-channel FET 428. The FET 428 has a drain connected to the positive potential system power supply (not shown) through a resistor 429 and a source connected to the system ground potential. The drain of the FET 428 is also connected to an inverting input 431-1 of an operational amplifier 431. A non-inverting input 431-2 is connected to the junction of a pair of resistors 432 and 433 through a resistor 434. The resistors 432 and 433 are connected in series between the positive potential system power supply (not shown) and the system ground potential to generate a reference voltage at the input 431-2. A positive power supply input 431-4 and a negative power supply input 431-5 are connected to the positive and negative system power supplies (not shown) respectively and a ground input 431-6 is connected to the system ground potential. A capacitor 435 is connected between the source and the drain of the FET 428.

When the signal at the collector of the transistor 414 is not changing, the NAND 419 will generate a "0"

which is changed to a "1" by the inverter 426. Assuming that the output 425-4 has been at "0", the FET 428 is turned on to apply the system power supply voltage to the input 431-1 and the amplifier functions as a comparator to generate the positive potential system power supply voltage as a "1" at the input 425-1. With both inputs at "1", the flip flop 425 is locked and will continue to generate a "0". If we further assume that the transistor 414 is turned on, the first signal transition will be from "0" to "1" as the transistor is turned off. The capacitor 418 will provide a "0" pulse at the input 419-1 and the capacitor 422 will provide a less than "0" pulse to the inverter 421 which will continue to generate a "1" at the input 419-2. The "0" pulse at the input 419-1 will generate a "1" pulse at the output 419-3 to set the flip flop 425 at the input 425-2 with a "0" pulse from the inverter 426. The output 425-3 will change from "1" to "0" and the output 425-4 will change from "0" to "1" to turn off the FET 428 and charge the capacitor 435. When the voltage across the capacitor 435 exceeds the reference voltage at the input 431-2, the output 431-3 will switch to the system ground potential to reset the flip flop with a "0" at the input 425-1. The output 425-3 will switch to "1" and the output 425-4 will switch to "0" to turn on the FET and quickly discharge the capacitor 435. The output 431-3 switches back to "1" and the flip flop 425 is again locked.

The second signal transition will be from "1" to "0" as the transistor 414 is turned on. The capacitor 418 will provide a greater than "1" pulse at the input 419-1 and the capacitor 422 will provide "1" pulse to the inverter 421 which will generate a "0" pulse at the input 419-2. The "0" pulse at the input 419-2 will generate a "1" pulse at the output 419-3 and the flip flop 425, FET 428 and amplifier 431 will cycle as discussed above. Therefore, the flip flop 425 will generate a train of constant width "0" pulses having a width determined by the time constant of the resistor 429 and capacitor 435.

The output 425-3 is connected to a terminal 436-1 of a switch 436 through an inverter 437. The inverter 437 will generate a train of constant width "1" pulses such that the average magnitude of the pulse train is proportional to the frequency of the pulse train on the 1000 PULSES input line 45-4. If the pulse train frequency is proportional to the machine cycle time, the average magnitude of the signal at the terminal 436-1 will also be proportional to the cycle time. An input 436-2 of the switch 436 is connected to a tap of a potentiometer 438 connected between a pair of resistors 439 and 441. The resistor 439 has its other end connected to positive potential power supply (not shown) and the resistor 441 has its other end connected to the system ground potential to generate a reference voltage having a magnitude proportional to a predetermined selected machine speed. The potentiometer 438 and the resistors 439 and 441 are located in the control circuit 42 of FIG. 1. An arm of the switch 436 can be connected to the 436-1 terminal during automatic operation of the inspection machine or can be connected to the 436-2 terminal during manual operation of the inspection machine.

The arm of the switch 436 is connected to a non-inverting input 442-2 of an operational amplifier 442 through a resistor 443 and a capacitor 444 is connected between the input 442-2 and the system ground potential. The resistor 443 and the capacitor 444 function as a low pass filter for the speed of rotation signal to provide a d.c. signal at the input 442-2. The amplifier 442 has an inverting input 442-1 internally connected to an output 442-3 for negative feedback and a positive 442-4 and a negative 442-5 power supply inputs connected to the positive and negative potential system power supplies (not shown) respectively. The output 442-3 is connected to the system ground potential through a potentiometer 445 and a resistor 446 connected in series. The potentiometer 445 and the resistor 446 are located in the control circuit 42 of FIG. 1. A tap of the potentiometer 445 is connected to a non-inverting input 447-2 of an operational amplifier 447 through a resistor 448. A capacitor 449 is connected between the input 447-2 and the system ground potential and the resistor 448 and the capacitor 449 function as a low pass filter. The tap of the potentiometer 445 is adjusted to compensate for differences in gearing ratios between the spinner pad 22 and the motor 24 for different inspection machines so that the signal generated at the input 447-2 is proportional to the average speed of rotation of the spinner pad.

The amplifier 447 has an inverting input 447-1 connected to an output 447-3 for negative feedback and a positive 447-4 and a negative 447-5 power supply inputs connected to the positive and negative potential system power supplies (not shown) respectively. A capacitor 451 is connected between a pair of inputs 447-6 and 447-7 to provide frequency compensation. The signal generated at the output 447-3 is the VA signal which is a positive potential signal, having a magnitude directly proportional to the speed of rotation of the container, which is applied to the output line 45-7 connected to the output 447-3.

The output 447-3 is also connected to the system ground potential through a potentiometer 452 and a resistor 453 connected in series. The potentiometer 452 and the resistor 453 are located in the control circuit 42 of FIG. 1. A tap of the potentiometer 452 is connected to a non-inverting input 454-2 of an operational amplifier 454 through a resistor 455. A capacitor 456 is connected between the input 454-2 and the system ground potential and the resistor 455 and the capacitor 456 function as a low pass filter. An inverting input 454-1 is connected to an output 454-3 through a resistor 457 for negative feedback and to the system ground potential through a resistor 458. A positive 454-4 and a negative 454-5 power supply inputs are connected to the positive and negative potential system power supplies (not shown) respectively. A capacitor 459 is connected between a pair of inputs 454-6 and 454-7 for frequency compensation. The potentiometer 452 is adjusted to compensate for different container body diameters such that the amplifier 454 generates the VD signal which has a magnitude proportional to the rotational speed and diameter of the container. The output 454-3 is connected to the output line 45-8 to output the VD signal.

The interface circuit 45 also includes a circuit which is responsive to the channel output signals for rejecting a container. An eight input NAND 461 has three inputs 461-1, 461-2 and 461-3 connected to the positive potential system power supply (not shown) to maintain them at "1". An input 461-4 is connected to an EXTERNAL REJECT line 45-5 and to the positive potential system power supply through a resistor 462. The CHANNEL ONE line 43-7 and the CHANNEL TWO line 43-5 from the circuit of FIG. 9, the CHANNEL THREE line 43-10 from the circuit of FIG. 11 and the CHANNEL FOUR line 43-14 from the circuit of FIG. 12 are each connected to a −2 terminal of separate switches for selecting one or more of these signals to reject containers. The line 43-7 is connected to a terminal 463-2 of a switch 463 having an arm connected to an input 461-5. The line 43-5 is connected to the input 461-6 through a terminal 464-2 and arm of a switch 464, the line 43-10 is connected to the input 461-7 through a terminal 465-2 and arm of a switch 465 and the line 43-14 is connected to an input 461-8 through a terminal 466-2 and arm of a switch 466. The switches each have a −1 terminal connected to the positive potential system power supply (not shown) to apply a "1" to the associated NAND 461 input wherein the switch arm can be switched to the −1 terminal when it is desired not to reject a container on one of the channel signals.

When there are no defects or an EXTERNAL REJECT signal, the input lines 45-5, 43-7, 43-5, 43-10 and 43-14 are at "1" and the NAND 461 generates a "0" at an output 461-9. The output 461-9 is connected to a REJECT signal line 45-9 through an inverter 467 to generate a "0" representing the absence of a REJECT signal. The output 461-9 is also connected to a base of a NPN transistor 468 having a collector connected to the positive potential system power supply (not shown) and an emitter connected to a base of a NPN transistor 469 through a resistor 471. The transistor 469 has a collector connected to a REJECT line 45-10 and an emitter connected to the system ground potential and to the base through a resistor 472. The "0" at the output 461-9 turns off the transistor 468 which turns off the transistor 469 to prevent current flow through an incandescent lamp 473 and a coil of an electromagnetic counter 474 connected in series between the positive potential system power supply (not shown) and the lead 45-10. The lamp 473 and the counter 474 are located in the indicators and counters circuit 39 of FIG. 1.

When one or more of the input signals to the NAND 461 goes to "0" a "1" is generated at the output 461-9. The line 45-5 can be connected to the REJECT output line of a second interface circuit where two detection systems are being used to inspect the same container. The EXTERNAL REJECT signal may go to "0" because the other circuit has rejected the container for a ribbon tear defect or one or more of the channel signals can go to "0" if a ribbon tear defect is detected. The "1" is changed to a "0" by the inverter 467 on the REJECT line 45-9 which line may be connected to a rejecting mechanism on the inspection machine. The "1" also turns on the transistors 468 and 469 to connect the line 45-10 to the system ground potential. Current will then flow to light the REJECT indicator lamp 473 and cycle the counter 474 which accumulates a total count of rejected containers.

In summary, the interface circuit 45 of FIG. 14 responds to an externally generated GUAGING signal to generate the GUAGE signal to enable the detector status circuit 38 to FIG. 6 and the detector channel circuits 43 of FIGS. 9, 11 and 12. The circuit also responds to an externally generated speed signal to generate the VA and VD reference signals to the detector channel circuits 43 of FIGS. 9 and 11 and the probe logic circuit 44 of FIG. 7. The circuit also responds to an EXTERNAL REJECT signal or one or more of the detector channel output signals to generate a REJECT signal, light a REJECT indicator lamp and cycle a counter of the total number of rejected containers.

The present invention concerns a detection circuit for use with an inspection machine including an inspection station for rotating a transparent container typically made from glass, a light source for illuminating the interior of the container and a detector assembly mounted adjacent the side wall of the container and having an upper and a lower light responsive means spaced apart along a line substantially parallel to the longitudinal axis of the container, each of the light responsive means generating an input signal with a characteristic proportional to the amount of light transmitted through the side walls of the container from the light source. The detection circuit monitors the input signals and generates an output signal in response to a predetermined change in the light proportional characteristic of the input signals, the output signal representing the detection of a predetermined type of defect.

The detection circuit includes amplifier means responsive to the input signals for generating amplified signals having the light proportional characteristics of the associated input signals. The amplifier means can include an individual amplifier circuit for each of the input signals with a pre-amplifier for pre-amplifying the input signal, a logarithmic amplifier for logarithmically amplifying the pre-amplified signal and an amplifier for amplifying the logarithmically amplified signal to generate the amplified signal. The amplified signals can have a first signal component representing the average input signal magnitude generated by the transmission of the light through an unobstructed side wall of the container and a second signal component representing the percentage deviation from the average magnitude generated by the transmission of light through an obstruction in the side wall of the container. The detection circuit can include filter means responsive to the amplified signals for separating the first signal components from the associated second signal components.

The detection circuit can also include comparison means for generating one or more reference signals, for comparing the light proportional characteristic or magnitude of the separated second signal component of the amplified signal with a reference signal and for generating a detection signal if a predetermined relationship exists between the light proportional characteristic and the reference signal or the magnitude of the separated second signal component exceeds the magnitude of the reference signal.

The detection circuit further includes a logic circuit means responsive to the detection signals for generating a signal having a duration representing a predetermined amount of rotation of the container and the logic circuit means is responsive to the detection signals during the duration of the timing means signal for generating the output signal. The logic circuit monitors the detection signal for four conditions: (1) At least one of the light responsive means generates an input signal with its light proportional characteristic representing at least an average deviation for the average magnitude; (2) A second input signal is generated within 150° of rotation of the first; (3) The duration of the input signal exceeds a predetermined distance measured along the circumference of the container; and (4) Both light responsive means do not generate input signals simultaneously. If the first condition and any of the other conditions are present, the logic circuit will generate the output signal.

The logic circuit includes four channel detector circuits. The first circuit is responsive to detection signals which satisfy the first and third conditions. The logic circuit means is responsive to the generation of a first one of the detection signals for generating the timing signal wherein the timing signal is initiated after a first predetermined time delay, typically two tenths of an inch of rotation of the container, and is terminated after a second predetermined time delay, typically seven tenths of an inch of rotation of the container, with both time delays being measured from the time of generation of the first detection signal. If a second detection signal is generated during the duration of the timing signal, the output signal is generated. Thus, the channel one detector circuit detects relatively wide defects which exceed the width of the normal seam.

The second circuit is responsive to detection signals which satisfy the first two conditions. The logic circuit means is responsive to the generation of a first one of the detection signals for generating the timing signal wherein the timing signal is initiated after the second predetermined time delay typically seven tenths of an inch of rotation of the container, and is terminated after a third predetermined time delay, typically 150° of rotation, with both time delays being measured from the time of generation of the first detection signal. If a second detection signal is generated during the duration of the timing signal, the output signal is generated. Since seams are located approximately 180° from each other, the channel two detection circuit detects a defect located within 150° of a seam but will not reject upon the detection of two seams.

The third and fourth circuits are responsive to detection signals which satisfy the first and fourth conditions. The logic circuit means is responsive to the generation of a first one of the detection signals for generating the timing signal wherein the timing signal is initiated at the time of the generation of the first detection signal and is terminated after the first time delay, typically two tenths of an inch of rotation of the container measured from the time of generation of the first detection signal. If, during the duration of the timing signal, one of the detection signals is generated for less than a predetermined amount of time, the third circuit generates the output signal. Thus the third circuit detects a defect which is short and may or may not be adjacent a seam.

The fourth circuit monitors the detection signals at three reference levels for large, average and small deviations. Each light responsive means generates a pair of input signals which in turn can generate a pair of detection signals. If, during the duration of the timing signal at least one of large detection signals is generated, at least a pair of the average detection signals are generated and no more than two of the small detection signals are generated, the fourth circuit will generate the output signal. Thus, the channel four detection circuit detects a short defect or a defect having a portion skewed beyond the two tenths of an inch.

The present invention also provides a method for inspecting a glass container which is rotated about its vertical axis and has its interior illuminated by a light source. The method includes generating a first signal having a magnitude proportional to the amount of light transmitted through the side wall of the container for at least two spaced apart positions along a line substantially parallel to the longitudinal axis of the container; generating a second signal having a magnitude representing the percentage deviation from the average magnitude of each of the first signals in response to the transmission of the light through an obstruction in the side wall; comparing the magnitudes of the second signals with the magnitude of a reference signal; generating a timing signal having a duration representing a predetermined amount of rotation of the container after a first one of the detection signals is generated; and generating an output signal representing the detection of a predetermined type of defect in response to the receipt of at least one of the detection signals during the duration of the timing signal. The step of generating the first signals can include generating the first signals for two pairs of positions and the step of generating a timing signal can include generating first, second and third timing signals defined by first, second and third time delays respectively measured from the generation of the first one of the detection signals. The step of generating the output signal is performed if there is a difference of a predetermined amount between the lengths of time the two pairs of detection signals are generated during the duration of the first timing signal, at least two of the detection signals are generated during the duration of the second timing signal or if the detection signals corresponding to at least one of the pairs of positions are generated during the duration of the third timing signal.

The step of comparing can include comparing the magnitudes of the second signals with the magnitudes of each of first through fourth reference signals representing large, average and small reduction and small increase percentage deviations respectively from the average magnitude of the first signals. The step of generating a detection signal includes generating first through fourth detection signals when the magnitudes of each of the second signals exceeds the magnitude of the first through fourth reference signals respectively. The step of generating the output signal is then performed if at least one of the first detection signals, the second detection signals from at least one of the pairs of positions and no more than two of either the third or fourth detection signals are generated during the duration of the first timing signal.

In accordance with the provisions of the patent statutes, the principle and mode of operation of the invention have been explained and illustrated in its preferred embodiment. However, it must be understood that the invention may be practiced otherwise than as specifically illustrated and described without departing from its spirit or scope.

What is claimed is:

1. In an inspection apparatus including an inspection station for rotating a glass container about its longitudinal axis, a light source for illuminating the interior of the glass container, a detector assembly mounted adjacent the side wall of the container and having light responsive means spaced apart along a line substantially parallel to the longitudinal axis of the container for generating at lease two input signals with a characteristic proportional to the amount of light transmitted through the side wall from the light source and a detection circuit for monitoring the input signals and for generating an output signal in response to a predetermined change in the light proportional characteristic of the input signals, the output signal representing the detection of a predetermined type of defect, the detection circuit comprising:

amplifier means responsive to the input signals for generating amplified signals having a first signal component representing the average light proportional characteristic of the input signal generated by the transmission of the light through an unobstructed side wall of the container and a second signal component representing the percentage deviation from the average characteristic generated by the transmission of light through an obstruction in the side wall of the container;

filter means responsive to said amplified signals for separating each of said first signal components from said associated second signal component;

comparison means for generating a reference signal, for comparing the light proportional characteristic of each of said separated second signal components with said reference signal and for generating a detection signal for each of said separated second signal components having a light proportional characteristic exceeding the magnitude of said reference signal; and logic circuit means including timing means responsive to said detection signals for generating a signal having a duration representing a predetermined amount of rotation of the container after a first one of said detection signals is received, said logic circuit means being responsive to said detection signals and said timing means signal for generating the output signal in response to the receipt of at least one of said detection signals during the duration of said timing means signal.

2. A detection circuit according to claim 1 wherein said amplifier means includes a logarithmic amplifier means responsive to the input signals for generating said amplified signals wherein each of said amplified signals represents the logarithm of said first and second signal components.

3. A detection circuit according to claim 1 wherein said first signal component represents the d. c. component and said second signal component represents the a. c. component of said input signals and said filter means is a high pass filter connected between said amplifier means and said comparing means for blocking said first signal component and passing said second signal component.

4. A detection circuit according to claim 1 wherein said comparison means includes an operational amplifier having one input connected to a source of said reference signal and another input connected to said filter means for receiving said separated second signal component for generating a comparator output signal at a first logic level when the magnitude of said separated second signal component is less than or equal to the magnitude of said reference signal and for generating said detection signal at a second logic level when the magnitude of said separated second signal component exceeds the magnitude of said reference signal.

5. A detection circuit according to claim 1 wherein said timing means is responsive to the receipt of a least one of said detection signals for generating said timing means signal with a duration representing the rotation of the container through 150° and said logic circuit means is responsive to the receipt of at least one of said detection signals during the duration of said timing means signal for generating the output signal.

6. A detection circuit according to claim 1 wherein said timing means is responsive to the receipt of at least one of said detection signals for generating said timing means signal with a duration representing the rotation of the container through a predetermined circumferential distance spaced from the point at which the first one of said detection signals was generated and said logic circuit means is responsive to the receipt of at least one of said detection signals during the duration of said timing means signal for generating the output signal.

7. A detection circuit according to claim 6 wherein said timing means signal is initiated approximately two tenths of an inch of circumferential distance from said point at which the first one of said detection signals was generated and is terminated approximately seven tenths of an inch of circumferential distance from said point.

8. A detection circuit according to claim 6 wherein said timing means signal is initiated approximately seven tenths of an inch of circumferential distance from said point at which the first one of said detection signals was generated and is terminated approximately at 150° of rotation of the container from said point.

9. A detection circuit according to claim 1 wherein the input signal generating means includes an upper light responsive means for generating a first one of said input signals and a lower light responsive means for generating a second one of said input signals, said timing means is responsive to the receipt of a detection signal generated by one of said first and second input signals for initiating said timing means signal and terminating said timing means signal after the container has rotated approximately two tenths of an inch of circumferential distance from the point at which the first one of said detection signals was generated, and said logic circuit means is responsive to a difference of a predetermined amount between the lengths of time of generation of said detection signals during the duration of said timing means signal for generating the output signal.

10. In an inspection apparatus including an inspection station for rotating a transparent container about its longitudinal axis, a light source for illuminating the interior of the container, a detector assembly mounted adjacent the side wall of the container and having light responsive means spaced apart along a line substantially parallel to the longitudinal axis of the container for generating at least one upper input signal and at least one lower input signal, each input signal with a characteristic proportional to the amount of light transmitted through the side wall from the light source and a detection circuit for monitoring the input signals and for generating an output signal in response to a predetermined change in the light proportional characteristic of the input signals, the output signal representing the detection of a predetermined type of defect, the detection circuit comprising:

amplifier means responsive to the upper and lower input signals for generating amplified signals having a first signal component representing the average light proportional characteristic of the corresponding one of the upper and lower input signals generated by the transmission of the light through an unobstructed side wall of the container and a second signal component representing the percentage deviation from the average light proportional characteristic of the corresponding one of the upper and lower input signals generated by the transmission of light through an obstruction in the side wall of the container;

filter means responsive to said amplified signals for separating each of said first signal components from said associated second signal component;

comparison means for generating reference signals, for comparing the light proportional characteristic of each of said separated second signal components with the magnitudes of at least two of said reference signals and for generating a detection signal for each of said separated second signal components having a light proportional characteristic which exceeds the magnitude of the one of said reference signals being compared, each of said reference signals having a different magnitude representing a percentage deviation from the average light proportional characteristic of the one of said input signals being compared;

logic circuit means including timing means responsive to said detection signals for generating a signal having a duration representing a predetermined amount of rotation of the container after a first one of said detection signals is received, said logic circuit means being responsive to said detection signals and said timing means signal for generating the output signal in response to the receipt of at least one of said detection signals during the duration of said timing means signal.

11. A detection circuit according to claim 10 wherein said timing means signal is initiated at a second point spaced a predetermined circumferential distance from a first point on the container side wall at which said first detection signal is received.

12. A detection circuit according to claim 11 wherein said timing means signal is initiated approximately seven tenths of an inch of circumferential distance from said first point and is terminated after approximately 150° of rotation from said first point.

13. A detection circuit according to claim 11 wherein said timing means signal is initiated approximately two tenths of an inch of circumferential distance from said first point and is terminated approximately seven tenths of an inch of circumferential distance from said first point.

14. A detection circuit according to claim 10 wherein said comparison means generates an upper and a lower detection signal when the magnitudes of said separated second signal components of said upper and lower input signals respectively exceed the magnitude of one of said reference signals representing an average percentage deviation from the average magnitudes of said upper and lower input signals and wherein said logic circuit means generates the output signal in response to a difference of a predetermined amount between the lengths of time of generation of said upper and lower detection signals during the duration of said timing means signal.

15. A detection circuit according to claim 10 wherein said comparison means generates an upper and a lower detection signal when the magnitudes of said separated second signal components of said upper and lower input signals respectively exceed the magnitude of one of said reference signals representing a relatively small percentage deviation from the average magnitudes of said upper and lower input signals and wherein said logic circuit means generates the output signal in response to the receipt of only one of said upper and lower detection signals during the duration of said timing means signal.

16. In an inspection apparatus including an inspection station for rotating a glass container about its longitudinal axis, a light source for illuminating the interior of the container, a detector assembly mounted adjacent the side wall of the container and having an upper pair and a lower pair of light responsive means spaced apart along a line substantially parallel to the longitudinal axis of the container, each of the light responsive means generating an input signal with a characteristic proportional to the amount of light transmitted through the side wall from the light source, and a detection circuit for monitoring the input signals and for generating an output signal in response to a predetermined change in the light proportional characteristic of the input signals, the output signal representing the detection of a predetermined type of defect, the detection circuit comprising:

amplifier means responsive to the input signals for generating amplified signals having the light proportional characteristic of the associated input signals;

comparison means for generating reference signals, for comparing the light proportional characteristic of said amplified signals with the magnitude at least one of said reference signals and for generating detection signals when a predetermined relationship exists between the light proportional characteristic of said amplified signals and the magnitude said reference signal; and logic circuit means responsive to said detection signals for generating a timing signal having a duration representing a predetermined amount of rotation of the container and for generating the output signal in response to the generation of at least one of said detection signals during the duration of said timing signal.

17. A detection circuit according to claim 16 wherein said amplifier means includes an individual amplifier circuit for each of the input signals.

18. A detection circuit according to claim 17 wherein each of said amplifier circuits includes a pre-amplifier means for pre-amplifying the associated one of the input signals, a logarithmic amplifier means for logarithmically amplifying said pre-amplified signal and an amplifier for amplifying said logarithmically amplified signal to generate one of said amplified signals.

19. A detection circuit according to claim 16 wherein said comparison means includes an individual comparison circuit for each of the amplified signals.

20. A detection circuit according to claim 19 wherein each of said comparison circuits includes filter means for separating the light proportional characteristic from the associated amplified signal for comparison with said reference signal.

21. A detection circuit according to claim 16 wherein said logic circuit means is responsive to the generation of at least a first one of said detection signals for generating said timing signal, said timing signal being initiated after a first predetermined time delay and being terminated after a second predetermined time delay to define the duration of said timing signal, said first and second time delays being measured from the time of generation of said first detection signal, and is responsive to the generation of said detection signals associated with the input signals generated by at least one of the paris of light responsive means during the duration of said timing signal for generating the output signal.

22. A detection circuit according to claim 21 wherein said first predetermined time delay represents approximately seven tenths of an inch of rotation of the container measured along the circumference of the container and said second predetermined time delay represents approximately 150 degrees of rotation of the container.

23. A detection circuit according to claim 21 wherein said first predetermined time delay represents approximately two tenths of an inch of rotation of the container and said second predetermined time delay represents approximately seven tenths of an inch of rotation of the container, said rotation being measured along the circumference of the container.

24. A detection circuit according to claim 16 wherein said logic circuit means is responsive to the generation of at least a first one of said detection signals for generating said timing signal, said timing signal being terminated after a predetermined time delay to define the duration of said timing signal, and is responsive to a difference of a predetermined amount between the length of time of generation of said detection signals associated with the input signals generated by the pairs of light responsive means during the duration of said timing signal for generating the output signal.

25. A detection circuit according to claim 24 wherein said predetermined time delay represents approximately two tenths of an inch of rotation of the container measured along the circumference of the container.

26. A detection circuit according to claim 16 wherein said comparison means generates at least three reference signals representing large, average and small deviations in the amount of light transmitted through the side wall of the container and generates first, second and third deviation signals when a predetermined relationship exists between the light proportional characteristic of said amplified signals and said large, average and small light deviation reference signal magnitudes respectively and wherein said logic signal means is responsive to the generation of at least a first one of said second deviation signals for generating said timing signal, said timing signal being terminated after a predetermined time delay to define the duration of said timing signal, and is responsive to the generation of at least one of said first deviation signals, at least two of said second deviation signals and no more than two of said third deviation signals during the duration of said timing signal for generating the output signal.

27. A detection circuit according to claim 26 wherein said predetermined time delay represents approximately two tenths of an inch of rotation of the container measured along the circumference of the container.

28. In an inspection apparatus including an inspection station for rotating a glass container about its longitudinal axis, a light source for illuminating the interior of the container, a detector assembly mounted adjacent the side wall of the container and having an upper pair and a lower pair of light responsive means spaced apart along a line substantially parallel to the longitudinal axis of the container, each of the light responsive means generating an input signal having a magnitude proportional to the amount of light transmitted through the side wall from the light source, and a detection circuit for monitoring the input signals and for generating an output signal in response to a predetermined change in the magnitude of one or more of the input signals, the output signal representing the detection of a predetermined type of defect, the detection circuit comprising:

means responsive to the input signals for generating signal components having magntidues representing the percentage deviation from the average magnitudes of each of the input signals, said deviations generated by the transmission of light through an obstruction in the side wall;

means for generating first through fourth reference signals having magnitudes representing large, average and small reduction and small increase percentage deviations respectively;

means for comparing said signal components with each of said reference signals and for generating first through fourth detection signals when the magnitudes of each of said signal components exceeds the magnitudes of said first through fourth reference signals respectively;

means for generating a first timing signal initiated by the generation of a first one of any of said first through fourth detection signals, terminated at the termination of a first time delay and having a duration representing a first predetermined amount of rotation, a second timing signal initiated at the termination of said first time delay, terminated at the termination of a second time delay and having a duration representing a second predetermined amount of rotation and a third timing signal initiated at the termination of said second time delay, terminated at the termination of a third time delay and having a duration representing a third predetermined amount of rotation; and means responsive to said timing signals and said detection signals for generating said output signal in response to difference of a predetermined amount between the lengths of time of generation of said second detection signals for the upper and lower pairs of light responsive means during the duration of said first timing signal, in response to the generation of at least said second detection signals corresponding to one of said pairs of light responsive means, the generation of at least one of said first detection signals and no more than two of either of said third and fourth detection signals during the duration of said first timing signal, in response to the generation of at least two of said second detection signals during the duration of said second timing signal, or in response to the generation of at least two of said second detection signals during the duration of said third timing signal.

29. A method for inspecting the side walls of a glass container wherein the container is rotated about its longitudinal axis and a light source illuminates the interior of the container comprising the steps of:

generating first signals having a magnitude representing the amount of light transmitted through the side wall of the container for at least two spaced apart positions along a line substantially parallel to the longitudinal axis of the container;

generating a second signal having a magnitude representing the percentage deviation from the average magnitude of each of said first signals in response to the transmission of the light through an obstruction in the side wall;

comparing the magnitudes of said second signals with the magnitude of a reference signal;

generating a detection signal when the magnitude of each of said second signals exceeds the magnitude of said reference signal;

generating a timing signal having a duration representing a predetermined amount of rotation of the container after a first one of said detection signals is generated; and generating an output signal representing the detection of a predetermined type of defect in response to the receipt of at least one of said detection signals during the duration of said timing signal.

30. The method accordng to claim 29 wherein the step of generating said timing signal includes initiating said timing signal at the termination of a first predetermined time delay and terminating said timing signal at the termination of a second predetermined time delay, said first and second time delays being measured from the generation of the first one of said detection signals.

31. The method according to claim 30 wherein said first time delay represents approximately two tenths of an inch of rotation of the container and said second time delay represents approximately seven tenths of an inch of rotation of the container, said rotation being measured along the circumference of the container.

32. The method according to claim 30 wherein said first time delay represents approximately seven tenths of an inch of rotation of the container measured along its circumference and said second time delay represents approximately 150° of rotation of the container.

33. The method according to claim 29 wherein the step of generating said timing signal includes initiating said timing signal at the generation of a first one of said detection signals and terminating said timing signal after approximately two tenths of an inch of rotation measured along the circumference of the container.

34. The method according to claim 33 wherein the step of generating said output signal is performed if there is a difference of a predetermined amount between the lengths of time said two detection signals are generated during the duration of said timing signal.

35. The method according to claim 33 wherein the step of generating said output signal is performed if at least one of said detection signals is not generated during the duration of said timing signal.

36. The method according to claim 29 wherein the step of generating said first signals includes generating said first signals for two pairs of positions, each of said four positions being located along said line; wherein the step of generating a timing signal includes generating a first timing signal initiated by the generation of said first detection signal and terminated after a first time delay, the duration of said first timing signal representing a first predetermined amount of rotation; and wherein the step of generating said output signal is performed if there is a difference of a predetermined amount between the lengths of time the two pairs of said detection signals are generated during the duration of said first timing signal.

37. The method according to claim 36 wherein the step of generating said timing signal includes generating a second timing signal initiated at the termination of said first time delay and terminated after a second time delay, the duration of said second timing signal representing a second predetermined amount of rotation, and wherein the step of generating said output signal is performed if at least two of said detection signals are generated during the duration of said second timing signal.

38. The method according to claim 37 wherein the step of generating said timing signal includes generating a third timing signal initiated at the termination of said second time delay and terminated after third time delay, the duration of said third timing signal representing a third predetermined amount of rotation, and wherein the step of generating said output signal is performed if said detection signals corresponding to at least one of said pairs of positions are generated during the duration of said third timing signal.

39. The method according to claim 38 wherein the step of comparing includes comparing the magnitudes of said second signals with the magnitudes of each of first through fourth reference signals representing large, average and small reduction and small increase percentage deviations respectively from the average magnitude of said first signals; the step of generating a detection signal includes generating first through fourth detection signals when the magnitude of each of said second signals exceeds the magnitude of said first through fourth reference signals respectively; and wherein the step of generating said output signal is performed if at least said second detection signals from one of said pairs of positions are generated during the duration of said first timing signal and at least one of said first detection signals is generated and no more than two of either said third or fourth detection signals are generated during the duration of said first timing signal.

* * * * *